(12) United States Patent
Beebe et al.

(10) Patent No.: US 8,728,410 B2
(45) Date of Patent: May 20, 2014

(54) DEVICE FOR AND METHOD OF EXTRACTING A FRACTION FROM A BIOLOGICAL SAMPLE

(75) Inventors: David J. Beebe, Monona, WI (US);
Scott M. Berry, Madison, WI (US);
Richard Burgess, Madison, WI (US);
Lindsay Strotman, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 432 days.

(21) Appl. No.: 13/033,351

(22) Filed: Feb. 23, 2011

(65) Prior Publication Data
US 2011/0212509 A1 Sep. 1, 2011

(51) Int. Cl.
*B03C 1/02* (2006.01)

(52) U.S. Cl.
USPC ............ 422/527; 422/501; 436/177; 436/180

(58) Field of Classification Search
USPC ................... 422/500, 501, 527; 436/177, 180; 204/545, 557, 560, 660
See application file for complete search history.

(56) References Cited

U.S. PATENT DOCUMENTS

| | | | |
|---|---|---|---|
| 5,279,936 A | 1/1994 | Vorpahl | |
| 6,117,398 A | 9/2000 | Bienhaus et al. | |
| 7,820,454 B2 | 10/2010 | Su et al. | |
| 8,017,340 B2 | 9/2011 | Collier et al. | |
| 8,048,633 B2 | 11/2011 | Collier et al. | |
| 2004/0224380 A1 | 11/2004 | Chou et al. | |
| 2005/0112601 A1 | 5/2005 | Hassibi et al. | |
| 2005/0208548 A1 | 9/2005 | Block et al. | |
| 2006/0024824 A1 | 2/2006 | Woodside et al. | |
| 2007/0042396 A1 | 2/2007 | Park et al. | |
| 2008/0124779 A1 | 5/2008 | Oh et al. | |
| 2008/0226500 A1* | 9/2008 | Shikida et al. | 422/68.1 |
| 2009/0191594 A1* | 7/2009 | Ohashi | 435/91.2 |
| 2009/0246782 A1 | 10/2009 | Kelso et al. | |
| 2010/0273142 A1 | 10/2010 | Prins et al. | |
| 2010/0291666 A1 | 11/2010 | Collier et al. | |
| 2011/0053289 A1* | 3/2011 | Lowe et al. | 436/501 |

FOREIGN PATENT DOCUMENTS

WO 2006071770 7/2006
WO WO 2007/110779 A2 * 10/2007

OTHER PUBLICATIONS

"Development of an enzymatic reaction device using magnetic bead-cluster handling", Shikida et al, J. Micromech. Microeng. 16 (2006) 1875-1883.
"Controlled microfluidic interfaces", Atencia et al, Nature, vol. 437, Sep. 29, 2005, 648-655.
"Using wettability and interfacial tension to handle droplets of magnetic beads in a micro-chemical-analysis system", Shikida et al, Sensors and Actuators B 113 (2006) 563-569.

(Continued)

*Primary Examiner* — Paul Hyun
(74) *Attorney, Agent, or Firm* — Boyle Fredrickson, S.C.

(57) ABSTRACT

A device and method are provided for facilitating extraction of a fraction from a biological sample. The biological sample includes non-desired material and a fraction-bound solid phase substrate. The device includes an input zone for receiving the biological sample therein and a phase-gate zone for receiving an isolation buffer therein. An output zone receives a reagent therein. A force is movable between a first position adjacent the input zone and a second position adjacent the output zone. The force urges the fraction-bound solid phase substrate from the input zone, through the phase-gate zone and into the output zone.

4 Claims, 11 Drawing Sheets

(56) References Cited

OTHER PUBLICATIONS

"Droplet-based gene expression analysis using a device with magnetic force-based-droplet-handling system", Okochi et al, Journal of Bioscience and Bioengineering, vol. 109, No. 2, 2010, 193-197.

"On-chip polymerase chain reaction microdevice employing a magnetic droplet-manipulation system", Tsuchiya et al, Sensors and Actuators B 130 (2008) 583-588.

"Forced motion of a probe particle near the colloidal glass transition", Habdas et al, Europhys. Lett., 67(3), pp. 477-583 (2004).

* cited by examiner

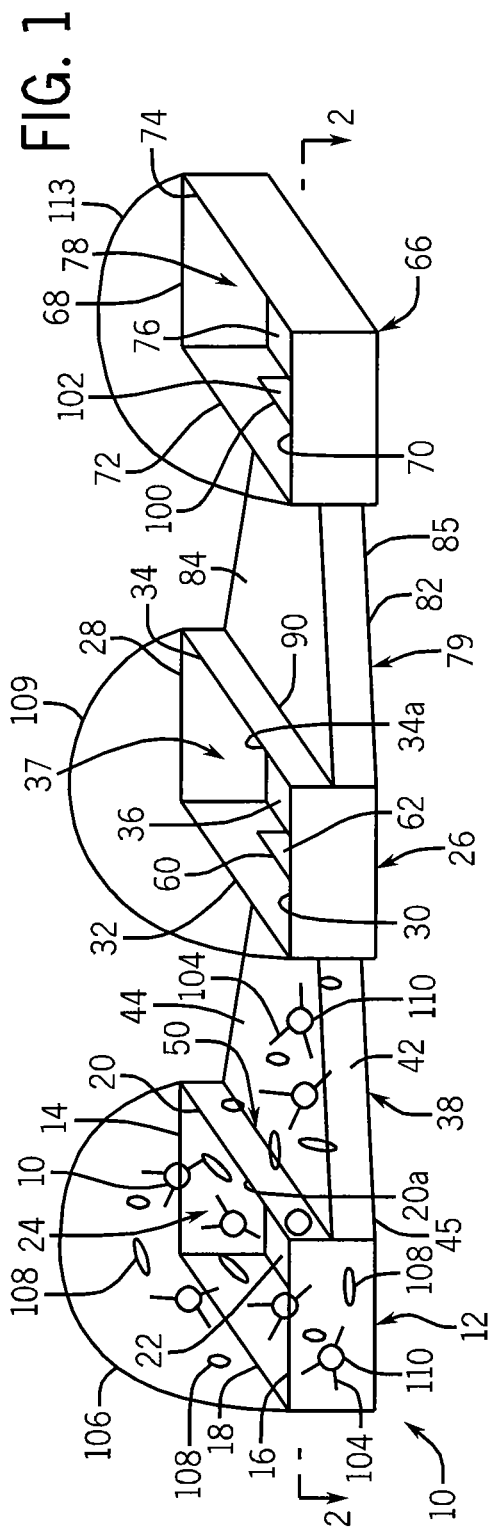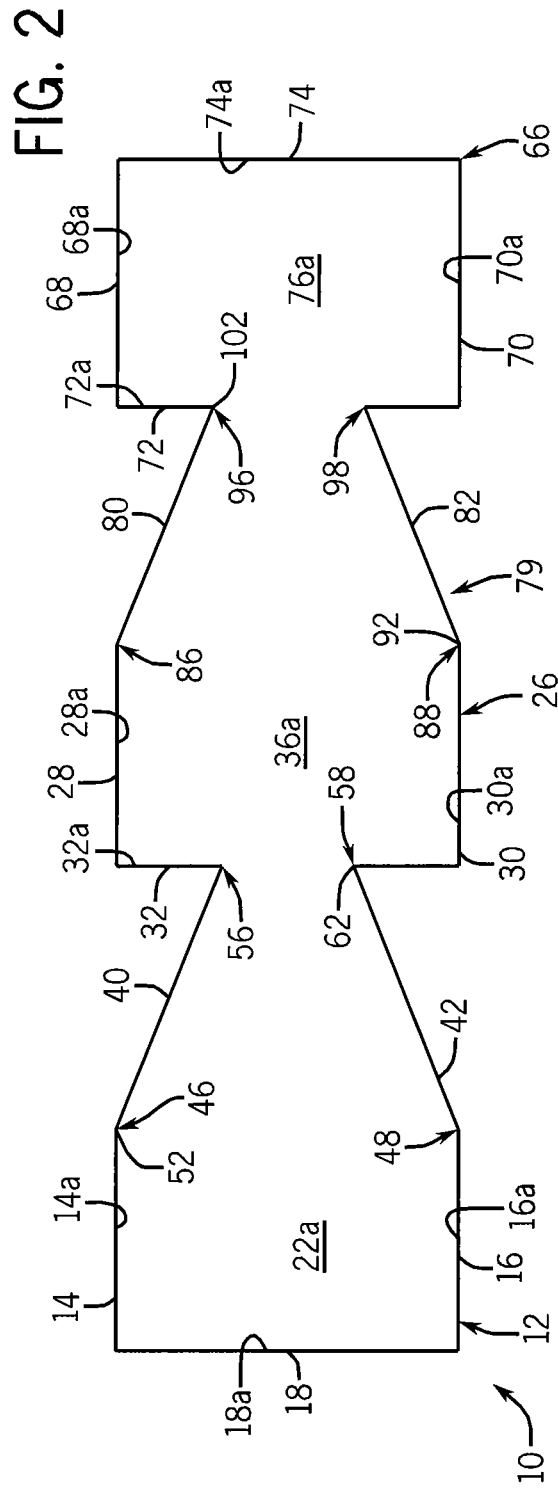

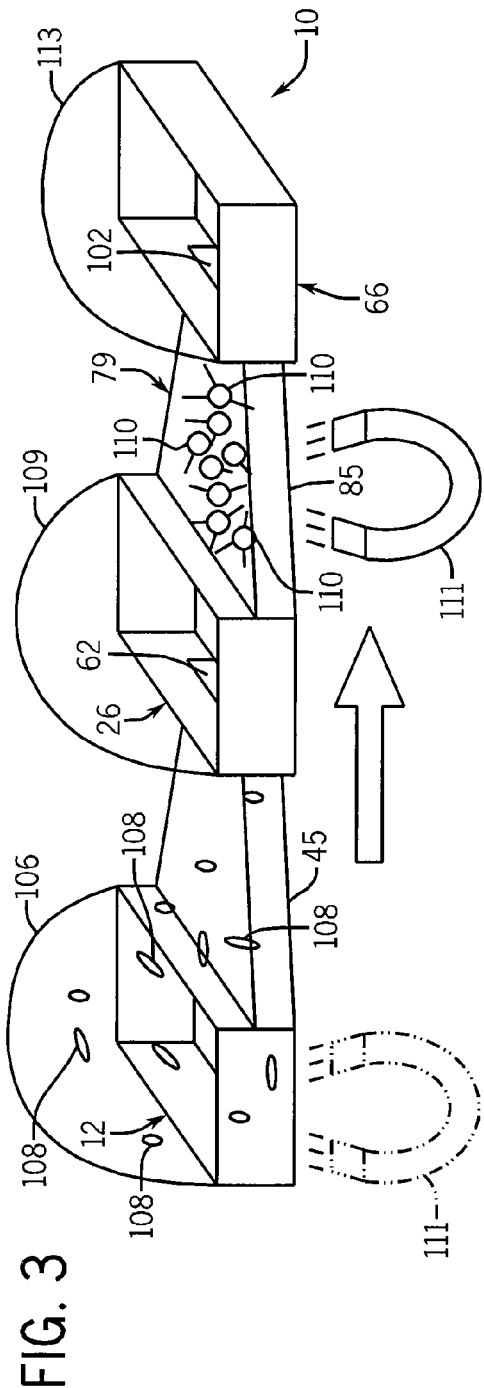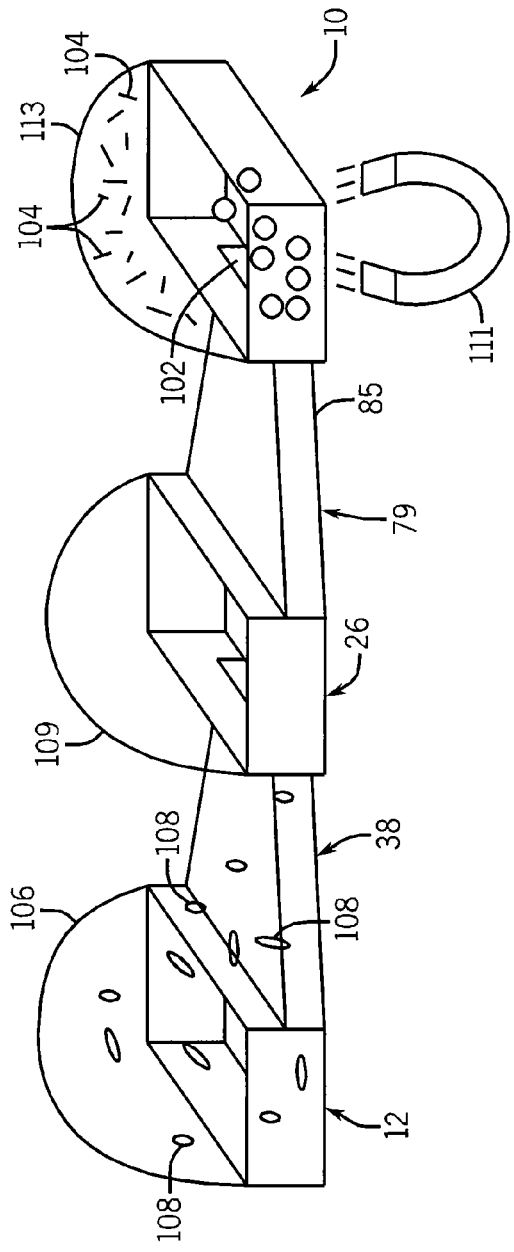

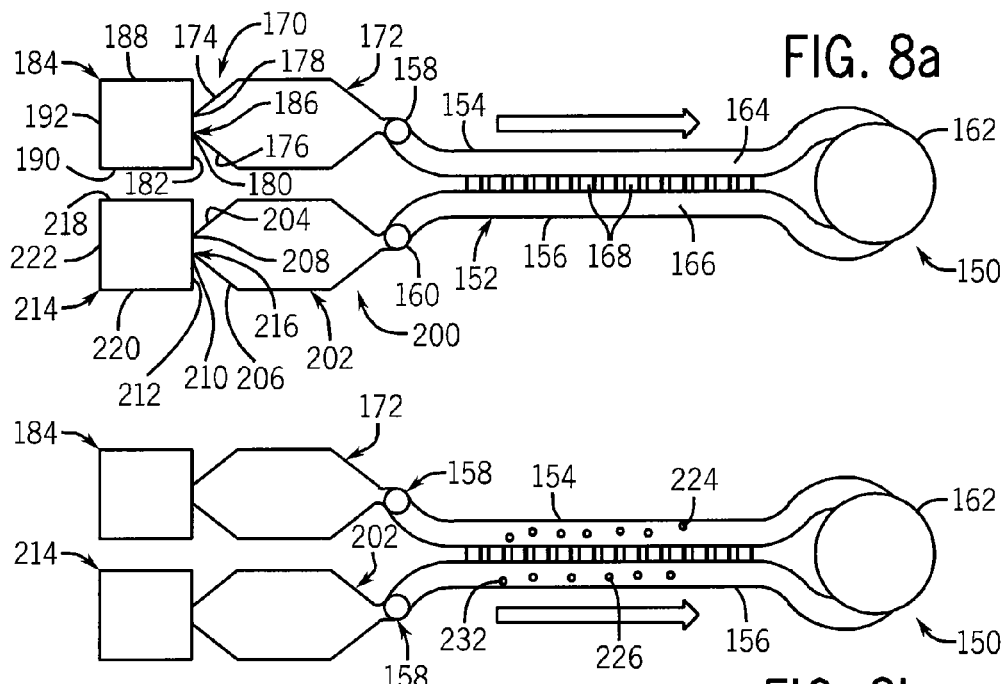
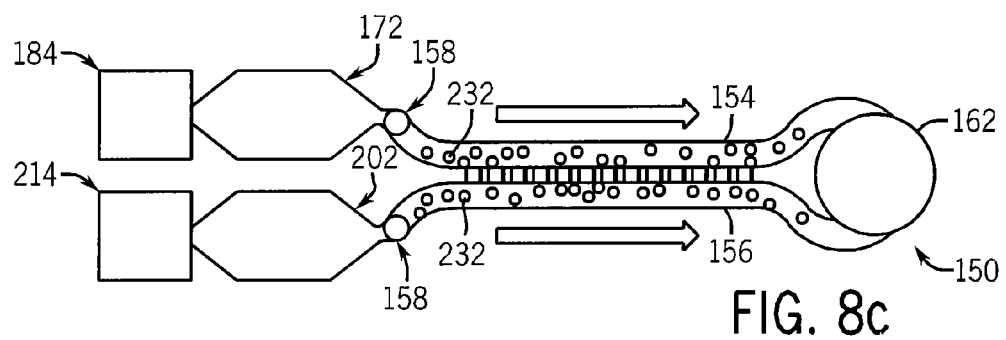
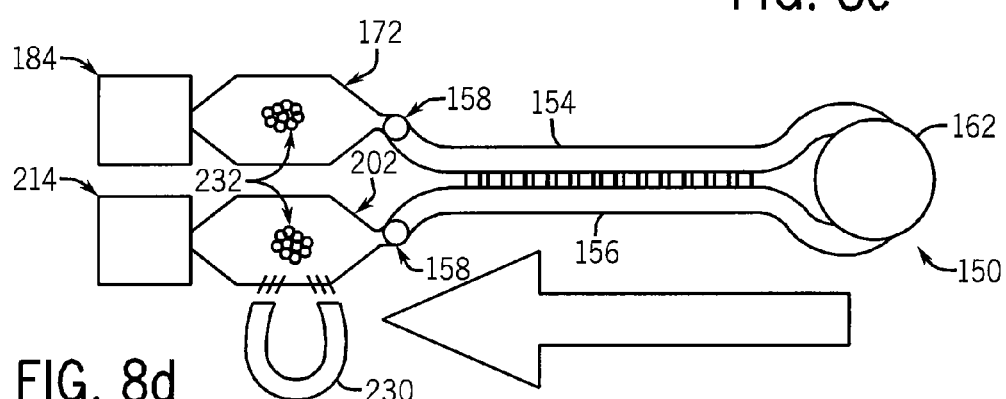
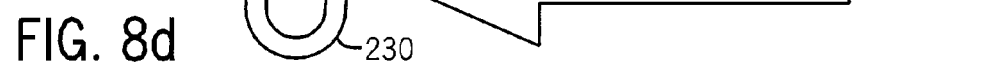

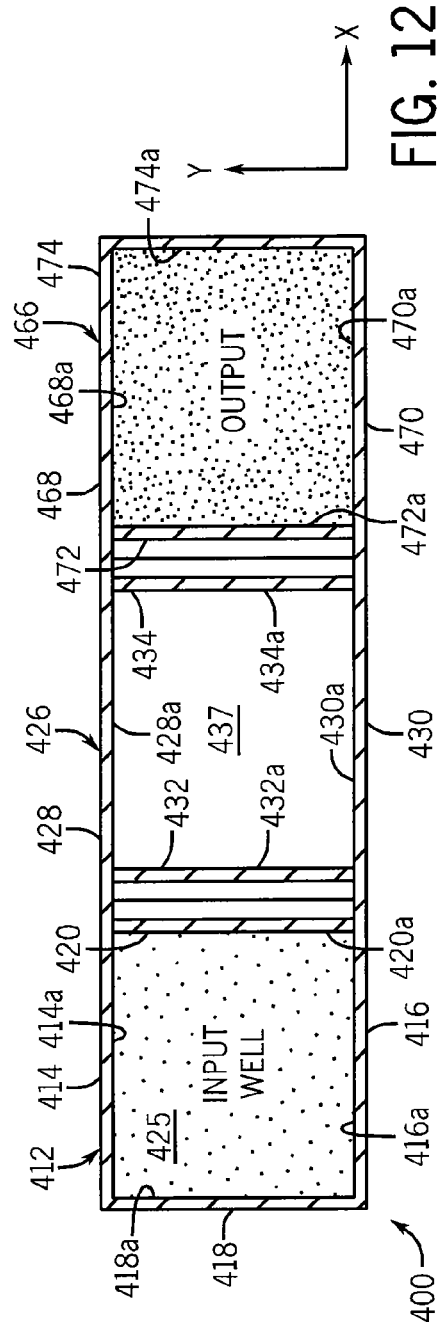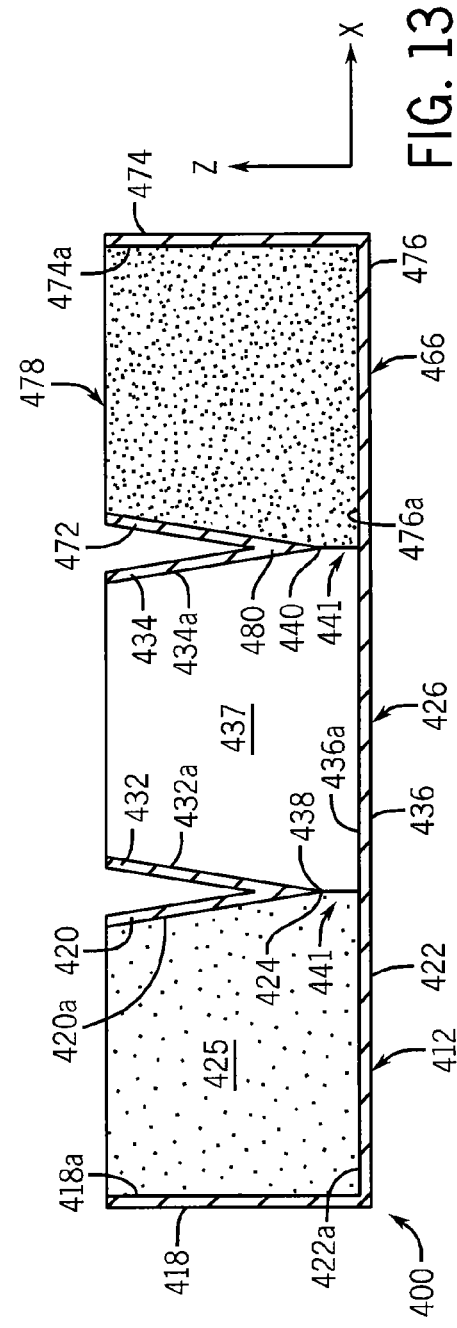

DEVICE FOR AND METHOD OF EXTRACTING A FRACTION FROM A BIOLOGICAL SAMPLE

FIELD OF THE INVENTION

The present invention relates generally to the extraction of nucleic acid and protein purification, and in particular, to a device for and a method of extracting a fraction from cultured cells, tissue samples and other biological materials.

BACKGROUND AND SUMMARY OF THE INVENTION

Effective isolation of nucleic acids from biological samples (e.g., cultured cells, tissue, viruses) is an essential prerequisite for efficient downstream amplification, detection, and quantification of specific genetic sequences via quantitative polymerase chain reaction (qPCR). The extraction process requires lysing the cells with harsh extraction reagents, such as detergents or enzymes, thereby resulting in a mixture of nucleic acids, cellular debris and extraction reagents. The nucleic acids are then separated/purified from the cellular debris and extraction reagents using a variety of techniques (e.g. organic solvent extraction, chromatography, centrifugation, dialysis). These techniques can be very time-consuming, tedious, and often require multiple washing steps. By way of example, commercially-available nucleic acid isolation kits require approximately 15 minutes to over one hour to complete, largely due to the multiple washing steps required to sufficiently separate the nucleic acids from the cellular debris and extraction reagents. Consequently, it has been suggested that as much as 15% of all molecular biology research time is devoted to purification.

In view of the foregoing, various attempts have been made to reduce the time associated with isolating nucleic acids from a biological sample. By way of example, Kelso, United States Patent Application No. 20090246782 discloses a system, device, and method for performing biological reactions. More specifically, the system contemplates placing a sample in a first chamber. The first chamber includes first processing reagents to generate a processed sample. The processed sample is moved through a water and alcohol immiscible, hydrophobic, or lipophilic barrier to a second chamber. The processed sample is treated in said second chamber with second processing reagents to generate a further processed sample.

While functional for its intended purpose, the system disclosed in the '782 application has certain limitations. For example, the reagents and immiscible phase of the system disclosed in the '782 application must be confined within corresponding chambers. As a result, the system requires the use of an external pump or two-axis magnet to move the processed sample between the chambers. It can be appreciated that the use of an external pump may have undesired effects on the sample. Alternatively, the use of a two-axis magnet may add unwanted cost and complexity to the system. In addition, the use of a plurality of chambers to isolate the nucleic acids from a biological sample may limit the throughput of the system.

Shikida et al., United States Patent Application No. 20080226500 discloses a miniaturized chemical analytic apparatus. The apparatus includes an introduction means for introducing a first droplet having a specimen therein into a liquid such that the structure of the first droplet is maintained. Magnetic ultrafine particles are mixed into the droplet while, once again, maintaining the structure thereof. It is contemplated for the specimens in the first droplet to bind to the particles. Thereafter, a magnetic field conveys the first droplet, with the specimen-bound magnetic particles therein, through the liquid to a desired location wherein the first droplet may be united with a second droplet for further processing downstream. The process may be repeated. A bulkhead may be provided between the areas wherein the first and second droplets are formed to maintain the droplets in such area.

It is noted that while the apparatus disclosed in the '500 application contemplates the movement of specimen-bound magnetic particles through a liquid for processing, no mechanism is provided for extracting the specimen-bound magnetic particles from the first droplet, or the droplets in which the first droplet subsequently merges. Hence, the apparatus and methodology disclosed in the '500 patent does not provide for an effective means for isolating particles, and their associated analyte(s), from a biological sample.

Therefore, it is a primary object and feature of the present invention to provide a device for and a method of extracting and purifying a fraction from cultured cells, tissue samples and other biological materials.

It is a further object and feature of the present invention to provide a device for and a method of extracting and purifying a fraction from cultured cells, tissue samples and other biological materials that is simpler and more efficient than prior devices and methods.

It is a still further object and feature of the present invention to provide a device for and a method of extracting and purifying a fraction from cultured cells, tissue samples and other biological materials that has higher throughput than prior devices and methods.

In accordance with the present invention, a device is provided for facilitating extraction of a fraction from a biological sample. The biological sample includes non-desired material and a fraction-bound solid phase substrate. The device includes an input zone for receiving the biological sample therein and a phase-gate zone for receiving an isolation buffer therein. An output zone receives a reagent therein. A force is movable between a first position adjacent the input zone and a second position adjacent the output zone. The force urges the fraction-bound solid phase substrate from the input zone, through the phase-gate zone and into the output zone.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 1 is an isometric view of a device in accordance with the present invention in an initial configuration;

FIG. 2 is a cross-sectional view of the device of the present invention taken along line 2-2 of FIG. 1;

FIG. 3 is an isometric view of a device of the present invention in a second configuration;

FIG. 4 is an isometric view of a device of the present invention in a third configuration;

FIGS. 8a-8d are schematic, top plan views of a co-culture platform incorporating a further embodiment of the device of the present invention wherein a series of operational steps associated with analyte purification is depicted;

FIG. 12 is a top plan view of a still further embodiment of a device in accordance with the present invention;

FIG. 13 is a side elevational view of the device of FIG. 12;

DETAILED DESCRIPTION OF THE DRAWINGS

Figure 5:
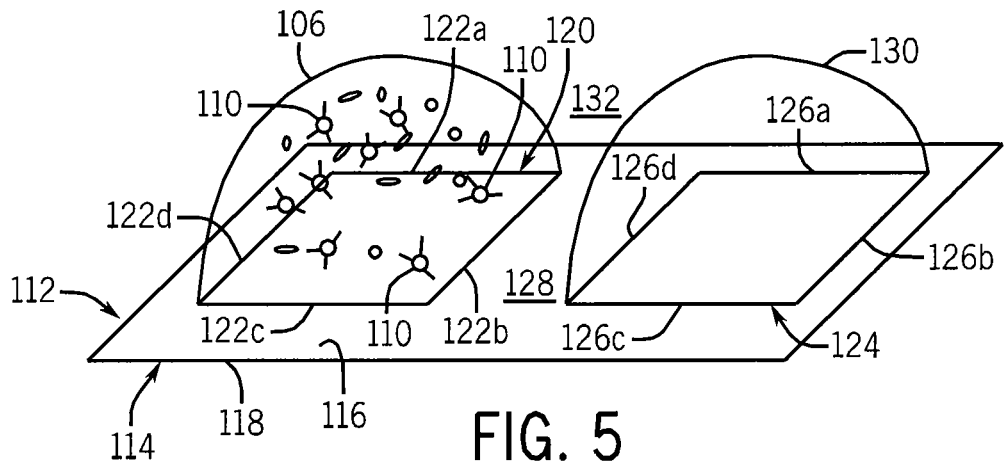
FIG. 5 is an isometric view of an alternate embodiment of a device in accordance with the present invention in an initial configuration.

Referring to FIGS. 1-4, a device for extracting and purifying a fraction from cultured cells, tissue samples and other biological materials in accordance with the present invention is generally designated by the reference numeral 10. Device 10 includes input zone or well 12 defined by first and second sidewalls 14 and 16, respectively, first and second end walls 18 and 20, respectively, and bottom wall 22. Inner surfaces 14a and 16a of sidewalls 14 and 16, respectively, inner surfaces 18a and 20a of first and second end walls 18 and 20, respectively, and upper surface 22a of bottom wall 22 define input cavity 24 for receiving a biological sample therein, as hereinafter described. While input well 12 has a generally rectangular configuration in the depicted embodiment, other configurations are contemplated without deviating from the scope of the present invention.

Device 10 further includes phase-gate zone or well 26 downstream of input well 12 and being defined by first and second sidewalls 28 and 30, respectively, upstream wall 32, downstream wall 34 and bottom wall 36. Inner surfaces 28a and 30a of sidewalls 28 and 30, respectively, inner surface 32a of upstream wall 32, inner surface 34a of downstream wall 34, and upper surface 36a of bottom wall 36 define phase-gate cavity 37 for receiving an isolation buffer therein, as hereinafter described. Again, although phase-gate well 26 has a generally rectangular configuration in the depicted embodiment, other configurations are contemplated without deviating from the scope of the present invention.

Input well 12 and phase-gate well 26 are interconnected by first channel 38. First channel 38 extends along an axis and is defined by first and second sidewalls 40 and 42, respectively, upper wall 44 and bottom wall 45. Input ends 46 and 48 of first and second sidewalls 40 and 42, respectively, of first channel 38 and input end 50 of upper wall 44 of input channel 38 intersect end wall 20 of input well 12 so as to define input 52 to first channel 38. Output ends 56 and 58 of first and second sidewalls 40 and 42, respectively, of first channel 38 and output end 60 of upper wall 44 of first channel 38 intersect upstream wall 32 of phase-gate well 26 so as to define output 62 of first channel 38. Bottom wall 45 of first channel 38 is generally co-planar with bottom walls 22 and 36 of input well 12 and phase-gate well 26, respectively. As best seen in FIG. 2, first and second sidewalls 40 and 42, respectively, of first channel 38 converge towards each other from input 52 to output 62, for reasons hereinafter described.

Device 10 further includes output zone or well 66 downstream of phase-gate well 26 and being defined by first and second sidewalls 68 and 70, respectively, upstream wall 72, downstream wall 74 and bottom wall 76. Inner surfaces 68a and 70a of sidewalls 68 and 70, respectively, inner surface 72a of upstream wall 72, inner surface 74a of downstream wall 74, and upper surface 76a of bottom wall 76 define output cavity 78 for receiving a reagent therein, as hereinafter described. Again, output well 66 has a generally rectangular configuration in the depicted embodiment, other configurations are contemplated without deviating from the scope of the present invention.

Output well 66 and phase-gate well 26 are interconnected by second channel 79. Second channel 79 extends along an axis and is defined by first and second sidewalls 80 and 82, respectively, upper wall 84 and bottom wall 85. Input ends 86 and 88 of first and second sidewalls 80 and 82, respectively, of second channel 79 and input end 90 of upper wall 84 of second channel 79 intersect downstream wall 34 of phase-gate well 26 so as to define input 92 to second channel 79. Output ends 96 and 98 of first and second sidewalls 80 and 82, respectively, of second channel 79 and output end 100 of upper wall 84 of second channel 79 intersect upstream wall 72 of output well 66 so as to define output 102 of second channel 79. Bottom wall 76 of second channel 79 is generally co-planar with bottom walls 36 and 76 of phase-gate well 26 and output well 66, respectively. As best seen in FIG. 2, first and second sidewalls 80 and 82, respectively, of second channel 79 converge towards each other from input 92 to output 102, for reasons hereinafter described.

In operation, it is intended to utilize device 10 to extract fraction 104, such as nucleic acids, whole cells and/or proteins, from biological sample 106. As is known, biological sample 106 may include non-desired material 108 such as lysate, bodily fluids, forensic samples, and/or biological contaminations. In order to prepare biological sample 106 for extraction of fraction 104, an appropriate reagent is added to biological sample 106 and mixed such that fraction 104 binds to a solid phase substrate in the reagent to form fraction-bound solid phase substrate 110. It is contemplated for the solid phase substrate to be attracted to a corresponding force. For example, the solid phase substrate may be a paramagnetic material attracted to a corresponding magnetic field. Other non-magnetic mechanisms such as gravity, ultrasonic actuation or the like are contemplated as being within the scope of the present invention. Once mixed with the reagent, biological sample 106 is deposited in input cavity 24 of input well 12; isolation buffer 109, such as oil or wax, is deposited in phase-gate cavity 37 of phase-gate well 26; and a desired reagent 113 is deposited in output cavity 78 of output well 66. It can be appreciated that the mixing of biological sample 106 and the reagent may occur in input cavity 24 of input well 12 and/or first channel 38 without deviating from the scope of the present invention.

Device 10 of the present invention and the other devices in accordance with the present invention described hereinafter rely upon the dominance of surface tension over gravity at the microscale to establish "virtual walls" between each fluid interface. This dominance of surface tension enables the side-by-side loading of fluids in the devices that is not possible on the macroscale. This phenomenon is quantified by the dimensionless Bond number:

$$Bo = \rho g L^2 / \gamma \qquad \text{Equation (1)}$$

wherein: Bo is the Bond number; $\rho$ is the density of a fluid; g is the acceleration of gravity; L is a characteristic length scale of the device; and $\gamma$ is the surface energy of the fluid.

A Bond number (Bo) less than 1 indicates a system in which surface tension forces are sufficiently large to marginalize the effects of gravity. For larger Bond number (Bo) devices, gravity dominance mandates positioning of the denser biological sample in input well 12 and reagent in output well 66 below the isolation buffer in phase-gate well 26, constraining device geometry into a three-dimensional architecture. Because Bond number (Bo) scales with the square of the characteristic length scale of the device ($L^2$), a reduction in device dimensions rapidly reduces the Bond number (Bo) into the surface tension-dominant regime. Microfluidic constrictions with very small characteristic length scales selectively impede liquid motion, enabling serial loading of all three device fluids (the biological sample, the isolation buffer and the reagent) into their respective wells (input well 12, phase-gate well 26 and output well 66, respectively) without intermixing or density-driven stratification. Hence, the reliance upon the dominance of surface tension, allow for the planarization of the layout of the devices of the present invention which, in turn, simplifies both device fabrication and operation while also enabling high-throughput arrays in well plate-like configurations.

In view of the foregoing, it is noted that the cross-sectional area of input 52 to first channel 38 is greater than the cross-sectional area of output 62 of first channel 38. As a result, biological sample 106 flows into first channel 38 through input 52 thereof. However, the surface tension of isolation buffer 109 in phase-gate cavity 37 of phase-gate well 26 at output 62 of first channel 38 prevents biological sample 106 from flowing into phase-gate cavity 37 of phase-gate well 26 through output 62 of first channel 38. Likewise, the surface tension of reagent 113 in output cavity 78 of output well 66 at output 102 of second channel 79 prevents isolation buffer 109 from flowing into output cavity 78 of output well 66 at output 102 of second channel 79.

In order to extract fraction-bound solid phase substrate 110 from biological sample 106, a force to which the solid phase substrate is attracted is positioned adjacent, and preferably below, input well 12. As heretofore described, it is contemplated for the solid phase substrate to be a paramagnetic material attracted to a corresponding magnetic field. As such, in order to generate the magnetic field, magnet 111 is positioned below input well 12 such that fraction-bound solid phase substrate 110 is magnetically attracted thereto. Magnet 111 is sequentially moved: 1) below bottom wall 45 of first channel 38 such that fraction-bound solid phase substrate 110 are drawn into first channel 38 through input 52 thereof; 2) below bottom wall 36 of phase-gate well 26 such that fraction-bound solid phase substrate 110 are drawn into phase-gate well 26 through output 62 of first channel 38; 3) below bottom wall 85 of second channel 79 such that fraction-bound solid phase substrate 110 are drawn into second channel 79 through input 92 thereof, FIG. 3; and 4) below bottom wall 76 of output well 66 such that fraction-bound solid phase substrate 110 are drawn into output well 66 through output 102 of second channel 79, FIG. 4. It is intended to move magnet 111 from its initial position below input well 12 to a position below output well 66 in less than 10 seconds. However, other time periods are contemplated as being within the scope of the present invention.

As previously noted, the surface tension of isolation buffer 109 in phase-gate cavity 37 of phase-gate well 26 at output 62 of first channel 38 prevents biological sample 106 from flowing into phase-gate cavity 37 of phase-gate well 26 through output 62 of first channel 38 and the surface tension of reagent 113 in output cavity 78 of output well 66 at output 102 of second channel 79 prevents isolation buffer 109 from flowing into output cavity 78 of output well 66 at output 102 of second channel 79. It can be appreciated that as fraction-bound solid phase substrate 110 passes through phase-gate well 26 and second channel 79, fraction-bound solid phase substrate 110 are washed by isolation buffer 109 therein, thereby effectively isolating fraction-bound solid phase substrate 110 from the remainder of biological sample 106. With fraction-bound solid phase substrate 110 isolated from the remainder of biological sample 106 in output well 66, fraction-bound solid phase substrate 110 may be treated in output well 66 by reagent 113 contained therein as desired by a user. In addition, it can be appreciated that output well 66 may be operatively connected to additional downstream components for further processing of fraction-bound solid phase substrate 110.

Figure 11A:
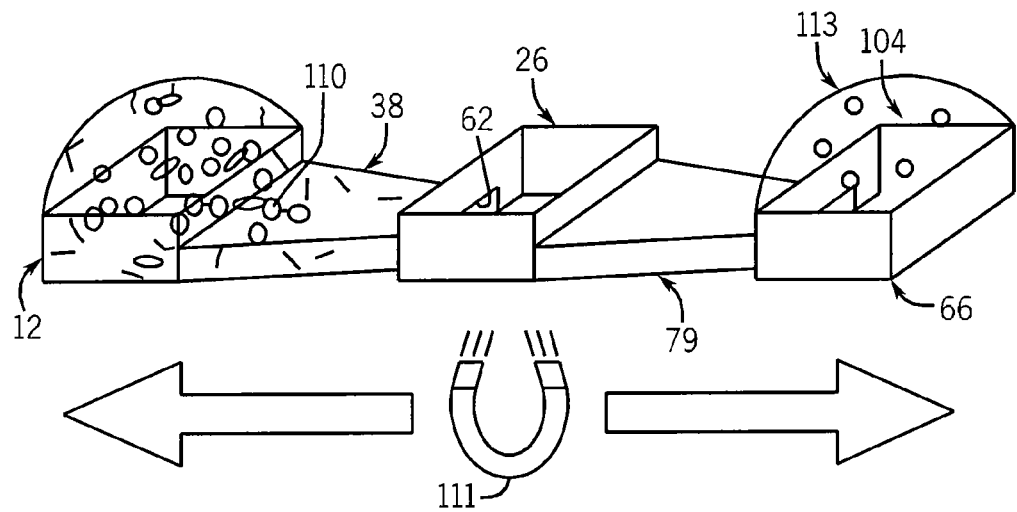
FIG. 11a is an isometric view of the device of the FIG. 1 in a still further configuration.

Referring to FIGS. 1 and 11*a*, it is contemplated for reagent 113 in output well 66 to be an elution buffer such that fraction 104 bound to the solid phase substrate may be extracted therefrom. Thereafter, the magnet 111 may be sequentially moved: 1) below bottom wall 85 of second channel 79 such that solid phase substrate are drawn into second channel 79 through output 102 of second channel 79; 2) below bottom wall 36 of phase-gate well 26 such that the solid phase substrate are drawn into phase-gate well 26 through input 92 to second channel 79; 3) below bottom wall 45 of first channel 38 such that solid phase substrate are drawn into first channel 38 through output 62 of first channel 38; and 4) below bottom wall 22 such that solid phase substrate are drawn into input well 12 through input 52 of first channel 38. With the solid phase substrate returned to input well 12, previously unbound fraction 104 in initial biological sample 106 remaining in input well 12 may now bind to a solid phase substrate to form additional fraction-bound solid phase substrate 110. Thereafter, the methodology heretofore described is repeated such that a substantial proportion of fraction 104 may be extracted from biological sample 106.

Figure 11B:
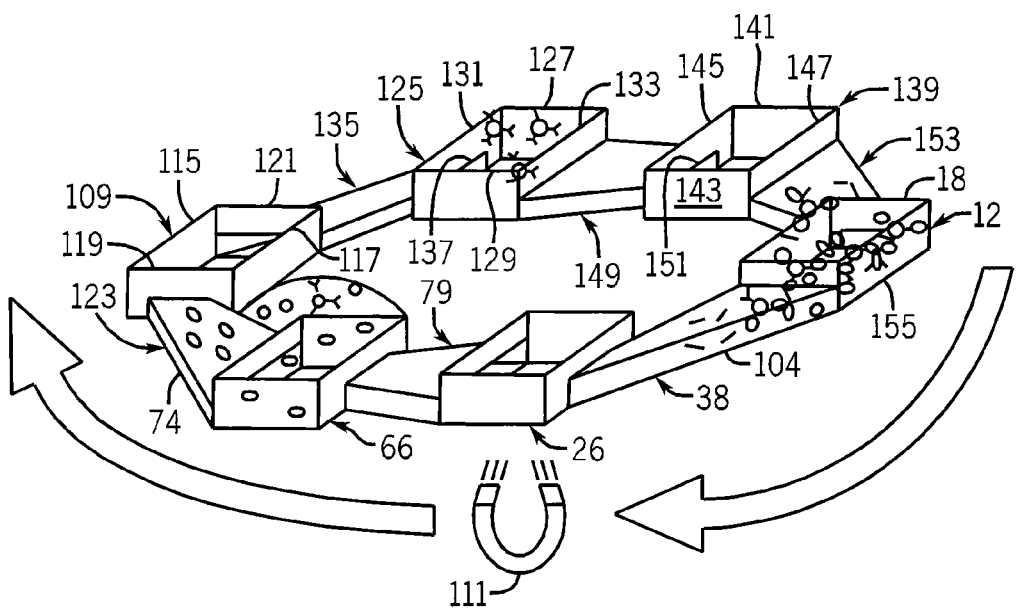
FIG. 11b is an isometric view of a still further embodiment of a device in accordance with the present invention.

It has been found that after several uses, the solid phase substrate may become contaminated with cell material. As a result, the capacity of the solid phase substrate to bind additional fraction 104 may drop. Referring to FIG. 11*b*, in order to overcome these limitations, it is contemplated to incorporate an arrangement for regenerating the capacity of the solid phase substrate. More specifically, second phase-gate zone or well 109 is provided downstream of output well 66 and being defined by first and second sidewalls 115 and 117, respectively, upstream wall 119, and downstream wall 121. The inner surfaces of sidewalls 115 and 117, respectively, the inner surface of upstream wall 119, and the inner surface of downstream wall 121 define a phase-gate cavity for receiving an isolation buffer therein, as heretofore described. Again, although second phase-gate well 109 has a generally rectangular configuration in the depicted embodiment, other configurations are contemplated without deviating from the scope of the present invention.

Output well 66 and second phase-gate well 109 are interconnected by third channel 123. Third channel 123 extends along an axis and is defined by first and second sidewalls, an upper wall and a bottom wall. The input ends of the first and second sidewalls of third channel 123 and the input end of the upper wall of third channel 123 intersect end wall 74 of output well 66 so as to define an input to third channel 123. The output ends of the first and second sidewalls of third channel 123 and the output end of the upper wall of third channel 123 intersect upstream wall 119 of phase-gate well 109 so as to define an output of third channel 123. The bottom wall of third channel 123 is generally co-planar with bottom walls 22 and 36 of input well 12 and phase-gate well 26, respectively. It can be seen that the first and second sidewalls of third channel 123 converge towards each other from the input to the output thereof, for reasons hereinafter described.

Wash zone or well 125 is provided downstream of second phase-gate well 109 and is defined by first and second sidewalls 127 and 129, respectively, upstream wall 131, and downstream wall 133. The inner surfaces of first and second sidewalls 127 and 129, respectively, the inner surface of upstream wall 131, and the inner surface of downstream wall 133 define a cavity for receiving a wash buffer therein, as hereinafter described. Again, wash well 125 has a generally rectangular configuration in the depicted embodiment, other configurations are contemplated without deviating from the scope of the present invention.

Wash well 125 and second phase-gate well 109 are interconnected by fourth channel 135. Fourth channel 135 extends along an axis and is defined by first and second sidewalls, an upper wall and bottom wall. The input ends of the first and second sidewalls of fourth channel 135 and the input end of the upper wall of fourth channel 135 intersect downstream wall 133 of second phase-gate well 109 so as to define an input to fourth channel 135. The output ends of the first and second sidewalls of fourth channel 135 and the output end of the upper wall of fourth channel 135 intersect upstream wall 131 of wash well 125 so as to define output 137 of fourth channel 135. The bottom wall of fourth channel 125 is generally co-planar with bottom walls second phase-gate well 109 and output well 66, respectively. It can appreciated that the first and second sidewalls of fourth channel 135 converge towards each other from the input to the output, for reasons hereinafter described.

Third phase-gate zone or well 139 is provided downstream of wash well 125 and is defined by first and second sidewalls 141 and 143, respectively, upstream wall 145, and downstream wall 147. The inner surfaces of sidewalls 141 and 143, respectively, the inner surface of upstream wall 145, and the inner surface of downstream wall 147 define a phase-gate cavity for receiving an isolation buffer therein, as heretofore described. Again, although third phase-gate well 139 has a generally rectangular configuration in the depicted embodiment, other configurations are contemplated without deviating from the scope of the present invention.

Wash well 125 and third phase-gate well 139 are interconnected by fifth channel 149. Fifth channel 149 extends along an axis and is defined by first and second sidewalls, an upper wall and a bottom wall. The input ends of the first and second sidewalls of fifth channel 149 and the input end of the upper wall of fifth channel 149 intersect downstream wall 133 of wash well 125 so as to define an input to fifth channel 149. The output ends of the first and second sidewalls of fifth channel 149 and the output end of the upper wall of fifth channel 149 intersect upstream wall 145 of third phase-gate well 139 so as to define output 151 of fifth channel 149. The bottom wall of fifth channel 149 is generally co-planar with bottom walls of wash well 125 and third phase-gate well 139, respectively. It can be seen that the first and second sidewalls of fifth channel 149 converge towards each other from the input to the output thereof, for reasons hereinafter described.

Third phase-gate well 139 and input well 12 are interconnected by sixth channel 153. Sixth channel 153 extends along an axis and is defined by first and second sidewalls, an upper wall and a bottom wall. The input ends of the first and second sidewalls of sixth channel 153 and the input end of the upper wall of fifth channel 153 intersect downstream wall 147 of third phase-gate well 139 so as to define an input to sixth channel 153. The output ends of the first and second sidewalls of sixth channel 153 and the output end of the upper wall of sixth channel 153 intersect first wall 18 of input well 12 so as to define output 155 of sixth channel 153. The bottom wall of sixth channel 153 is generally co-planar with bottom walls of input well 12 and third phase-gate well 139, respectively. It can be seen that the first and second sidewalls of sixth channel 153 converge towards each other from the input to the output thereof, for reasons hereinafter described.

In operation, it is contemplated for reagent 113 in output well 66 to be an elution buffer such that fraction 104 bound to the solid phase substrate may be extracted therefrom. In addition, an isolation buffer, such as oil or wax, is deposited in second and third phase-gate wells 109 and 139, respectively; and a stripping solution for cleaning/recycling the solid phase substrate is deposited in wash well 125. Thereafter, the magnet 111 may be sequentially moved: 1) below the bottom wall of third channel 123 such that solid phase substrate are drawn into third channel 123 through the input thereof; 2) below the bottom wall of second phase-gate well 109 such that solid phase substrate are drawn into second phase-gate well 109 through the output of third channel 123; 3) below the bottom wall of fourth channel 135 such that solid phase substrate are drawn into fourth channel 135 through the input thereof; 4) below the bottom wall of wash well 125 such that solid phase substrate are drawn into wash well 125 through output 137 of fourth channel 135; 5) below the bottom wall of fifth channel 149 such that solid phase substrate are drawn into fifth channel 149 through the input thereof; 6) below the bottom wall of third phase-gate well 139 such that solid phase substrate are drawn into third phase-gate well 139 through output 151 of fifth channel 149; 7) below the bottom wall of sixth channel 153 such that solid phase substrate are drawn into sixth channel 153 through the input thereof; and 7) below bottom wall 22 of input well 12 such that solid phase substrate are drawn into input well 12 through output 155 of sixth channel 153.

The surface tension of: 1) the isolation buffer in second phase-gate well 109 at output of third channel 123 isolates the solid phase substrate from fraction 104 and the elution buffer; 2) the stripping solution in wash well 125 prevents the isolation buffer in second phase-gate well 109 from flowing into wash well 125; and 3) the isolation buffer in third phase-gate well 139 isolates the stripping solution in wash well 125 from the biological sample 106 in input well 12. It can be appreciated that as solid phase substrate passes through wash well 125, the stripping solution cleans and/or recycles solid phase substrate such that when the solid phase substrate returns to input well 12, the previously unbound fraction 104 in initial biological sample 106 remaining in input well 12 may now bind to a solid phase substrate to form additional fraction-bound solid phase substrate 110. Thereafter, the methodology heretofore described may be repeated such that a substantial proportion of fraction 104 may be extracted from biological sample 106.

As described, the methodology of the present invention does not require any electronic equipment such as centrifuges, rockers/shakers, or incubators, while consuming only minimal volumes of reagents in the three wells. It can also be appreciated that the simplicity of device 10 allows for it to be easily reconfigured to form a mating relationship with the input/output requirements of upstream and downstream components.

Figure 6:
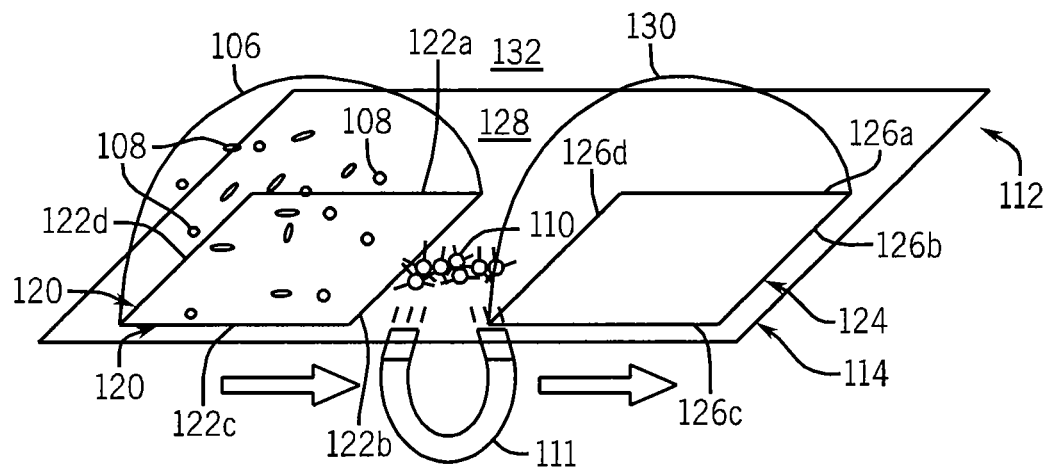
FIG. 6 is an isometric view of the alternate embodiment of the device in accordance with the present invention in a second configuration.

Referring to FIGS. 5-6, an alternate embodiment of the device for extracting and purifying a fraction from cultured cells, tissue samples and other biological materials in accordance with the present invention is generally designated by the reference numeral 112. Device 112 includes plate 114 having upper and lower surfaces 116 and 118, respectively. Except as hereinafter described, upper surface 116 of plate 114 is hydrophobic. Upper surface 116 of plate 114 includes a hydrophilic input zone 120 defined by edges 122a-122d such that input zone 120 has a generally square configuration. However, other configurations are contemplated as being within the scope of the present invention. In addition, upper surface 116 of plate 114 includes a hydrophilic output zone 124 defined by edges 126a-126d such that output zone 124 has a generally square configuration. However, other configurations are contemplated as being within the scope of the present invention. The portion of upper surface 116 of plate 114 outside of input zone 120 and output zone 124 defines hydrophobic isolation zone 128.

In operation, the mixture of biological sample 106 and a reagent, as heretofore described, is deposited on input zone 120 and a desired reagent 130 is deposited on output zone 124. Device 112 is flooded with isolation buffer 132 (e.g. oil, wax or the like) such that the mixture biological sample 106 and the reagent deposited on input zone 120 and desired reagent 130 deposited on output zone 124 are completely submerged in isolation buffer 132.

In order to extract fraction-bound solid phase substrate 110 from biological sample 106, a force to which the solid phase substrate of fraction-bound solid phase substrate 110 is attracted is positioned adjacent, and preferably below, input zone 120. In the exemplary embodiment, it is contemplated for the solid phase substrate of fraction-bound solid phase substrate 110 to be a paramagnetic material attracted to a corresponding magnetic field. As such, in order to generate the magnetic field, magnet 111 is positioned below input zone 120 such that fraction-bound solid phase substrate 110 is magnetically attracted thereto. Referring to FIG. 6, magnet 111 is sequentially moved: 1) below isolation zone 128 such that fraction-bound solid phase substrate 110 are drawn into isolation buffer 132; and 2) below output zone 124 such that fraction-bound solid phase substrate 110 are drawn into reagent 130.

It is noted that the surface tension of isolation buffer 132 deposited on isolation zone 128 prevents biological sample 106 flowing from input zone 120 into isolation zone 126. In addition, the surface tension of reagent 130 deposited on output zone 124 prevents isolation buffer 132 from flowing into output zone 124. It can be appreciated that as fraction-bound solid phase substrate 110 passes through isolation buffer 132 deposited on isolation zone 128, fraction-bound solid phase substrate 110 are washed by isolation buffer 132, thereby effectively isolating fraction-bound solid phase substrate 110 from the remainder of biological sample 106. With fraction-bound solid phase substrate 110 isolated from the remainder of biological sample 106 in reagent 130 deposited on output zone 124, fraction-bound solid phase substrate 110 may be acted on by reagent 130. In addition, it can be appreciated that reagent 130 may be operatively connected to additional downstream components for further processing of fraction-bound solid phase substrate 110.

Figure 7:
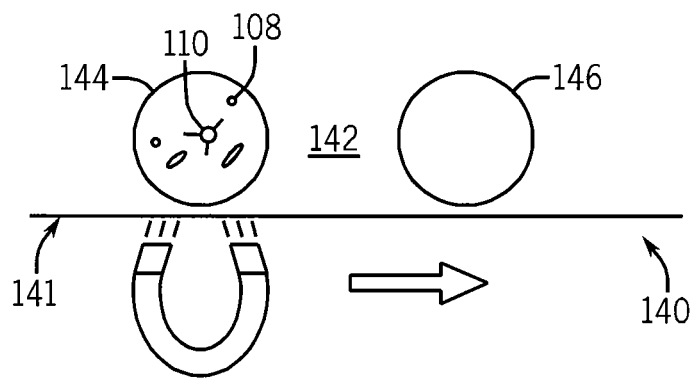
FIG. 7 is a schematic view of a still further embodiment of a device in accordance with the present invention in an initial configuration.

Referring to FIG. 7, a still further embodiment of a device for extracting and purifying a fraction from cultured cells, tissue samples and other biological materials in accordance with the present invention is generally designated by the reference numeral 140. Device 140 includes chamber 141 adapted for receiving isolation buffer 142 therein. Drop 144 of the mixture of biological sample 106 and a reagent, as heretofore described, is deposited in isolation buffer 142 so as to define an input zone. In addition, drop 146 of a desired reagent is deposited in isolation buffer 142 so as to define an output zone.

In order to extract fraction-bound solid phase substrate 110 from biological sample 106, a force to which the solid phase substrate of fraction-bound solid phase substrate 110 is attracted is positioned adjacent drop 144. In the exemplary embodiment, it is contemplated for the solid phase substrate of fraction-bound solid phase substrate 110 to be a paramagnetic material attracted to a corresponding magnetic field. As such, in order to generate the magnetic field, magnet 111 is positioned adjacent drop 144 such that fraction-bound solid phase substrate 110 is magnetically attracted thereto. Magnet 111 is moved from a position adjacent drop 144 to a position adjacent drop 146 such that fraction-bound solid phase substrate 110 are sequentially drawn: 1) into isolation buffer 142; and 2) into drop 146.

It is noted that the surface tension of isolation buffer 142 prevents biological sample 106 from passing out of drop 144 into isolation buffer 142. In addition, the surface tension of drop 146 prevents isolation buffer 142 from flowing into drop 146. It can be appreciated that as fraction-bound solid phase substrate 110 passes through isolation buffer 142, fraction-bound solid phase substrate 110 are washed by isolation buffer 142, thereby effectively isolating fraction-bound solid phase substrate 110 from the remainder of biological sample 106. With fraction-bound solid phase substrate 110 isolated from the remainder of biological sample 106, fraction-bound solid phase substrate 110 may be acted on by the reagent of drop 144. In addition, it can be appreciated that drop 144 may be operatively connected to additional downstream components for further processing of fraction-bound solid phase substrate 110.

Again, it is noted that the methodology of the present invention does not require any electronic equipment such as centrifuges, rockers/shakers, or incubators, while consuming only minimal volumes of reagents in the three wells. It can also be appreciated that the simplicity of device 140 allows for it to be easily reconfigured to form a mating relationship with the input/output requirements of upstream and downstream components.

Referring to FIGS. 8a-8d, a co-culture platform incorporating a further embodiment of the device of the present invention is generally designated by the reference numeral 150. It is intended for co-culture platform 150 to be used in isolating analytes or biomolecules directly from a cell culture. More specifically, co-culture platform 150 includes channel network 152 defined by first and second, channels 154 and 156, respectively. First and second channels 154 and 156, respectively, include inputs 158 and 160, respectively, and a common output 162. Input 158 of first channel 154 is connected to output 162 by central passageway 164. Similarly, input 160 of second channel 156 is connected to output 162 by central passageway 166. A series of diffusions ports 168 are axially spaced along and interconnect central passageways 164 and 166 of first and second channels 154 and 156, respectively, so as to allow for communication therebetween. For reasons hereinafter described, the absolute value of the radius of curvature of a droplet at output 162 is greater than the absolute values of the radii of curvature of droplets at inputs 158 and 160 of first and second channels 154 and 156, respectively.

Co-culture platform 150 further includes a first isolation device generally designated by the reference numeral 170. First isolation device 170 includes a phase-gate zone or well 172 communicating with first channel 154 at a location adjacent input 158 through an opening having a diameter substantially smaller than diameter of first channel 154 so as to form a constriction to fluid flow therethrough. Phase-gate well 172 is partially defined by first and second sidewalls 174 and 176, respectively, which converge toward each other and terminate at output ends 178 and 180, respectively. Output ends 178 and 180 of first and second sidewalls 174 and 176, respectively, of well 172 intersect upstream wall 182 of output zone or well 184 so as to define output 186 of phase-gate well 172. Output well 184 is downstream of phase-gate well 172 and communicates with phase-gate well 172 through output 186. Output well 184 is defined by first and second sidewalls 188 and 190, respectively, upstream wall 182 and downstream wall 192. As described, output well 184 has a generally rectangular configuration in the depicted embodiment. However, other configurations are contemplated without deviating from the scope of the present invention.

Co-culture platform 150 also includes a second isolation device generally designated by the reference numeral 200. Second isolation device 200 includes a phase-gate zone or well 202 communicating with second channel 156 at a location adjacent input 160 through an opening having a diameter substantially smaller than diameter of second channel 156 so as to form a constriction to fluid flow therethrough. Phase-gate well 202 is partially defined by first and second sidewalls 204 and 206, respectively, which converge toward each other and terminate at output ends 208 and 210, respectively. Output ends 208 and 210 of first and second sidewalls 204 and 206, respectively, of well 202 intersect upstream wall 212 of output zone or well 214 so as to define output 216 of phase-gate well 202. Output well 214 is downstream of phase-gate well 202 and communicates with phase-gate well 202 through output 216. Output well 214 is defined by first and second sidewalls 218 and 220, respectively, upstream wall 212 and downstream wall 222. As described, output well 214 has a generally rectangular configuration in the depicted embodiment. However, other configurations are contemplated without deviating from the scope of the present invention.

In operation, first and second channels 154 and 156, respectively, are filled with predetermined media. It can be appreciated that the high surface energy associated with the constricted opening between phase-gate well 172 and first channel 154 sequesters the media within first channel 154. Likewise, the high surface energy associated with the constricted opening between phase-gate well 202 and second channel 156 sequesters the media within second channel 156. These so-called "virtual walls" between first and second channels 154 and 156, respectively, and corresponding phase-gate wells 172 and 202 allow for fluid manipulation within first and second channels 154 and 156, respectively, without affecting first and second isolation devices 170 and 200, respectively.

It is noted that because the absolute value of the radius of curvature of the droplet at output 162 is greater than the absolute value of the radius of curvature of the droplet at input 158 of first channel 154, a larger pressure exists on input 158 of first channel 154. The resulting pressure gradient causes sequential droplets of culture media deposited on input 158 of first channel 154 to flow through central passageway 164 towards output 162, FIG. 8a. As such, in order to culture a first type of cells in first channel 154, it is contemplated to flow a suspension of the first cell type into first channel 154, as heretofore described. Similarly, because the absolute value of the radius of curvature of the droplet at output 162 is greater than the absolute value of the radius of curvature of the droplet at input 160 of second channel 156, a larger pressure exists on input 160 of second channel 156. Hence, the resulting pressure gradient causes sequential droplets of culture media deposited on input 160 of second channel 156 to flow through central passageway 166 towards output 162, FIG. 8b. As such, in order to culture a second type of cells in second channel 156, it is contemplated to flow a suspension of the second cell type into second channel 156, as heretofore described.

The first and second types of cells 224 and 226, respectively, are allowed to culture for a predetermined time period. In addition, isolation buffers, such as oil or wax, are deposited in phase-gate well 172 and in phase-gate well 202. Further, desired reagent/reaction buffers, such as real time, reverse transcription-polymerase chain reaction (RT/RT-PCR) reagents, are deposited in output wells 184 and 214. Lysis buffers spiked with solid phase substrates, such as mRNA-binding paramagnetic particles, are flowed into first and second channels 154 and 156, respectively, as heretofore described, FIG. 8c. After a predetermined time period, e.g. 5-20 minutes, to allow for lysis and the binding of the mRNA to the mRNA-binding paramagnetic particles, magnet 230 is positioned below central passageways 164 and 166 of first and second channels 154 and 156, respectively, such that the mRNA-bound paramagnetic particles 232 are magnetically attracted thereto. Magnet 230 is sequentially moved: 1) below phase-gate well 172 and in phase-gate well 202 such that the mRNA-bound paramagnetic particles 232 are drawn through the so-called "virtual walls" between first and second channels 154 and 156, respectively, and corresponding phase-gate wells 172 and 202 and into the isolation buffers; and 2) below output wells 184 and 214 such that the mRNA-bound paramagnetic particles 232 are drawn into RT/RT-PCR reagents. It can be appreciated that the co-culture platform 150 and the methodology heretofore described allow a user to isolate nucleic acids or other biomolecules directly from cell culture (s) without transferring lysate from a cell culture platform to a separate and distinct isolation platform. Further, the co-culture platform 150 and the methodology heretofore described is easily amenable to arrayed fabrication and operation, thereby facilitating the acceleration of analysis throughput.

Referring to FIGS. 1 and 9a-9e, a device for quantifying a level of a specific particle/protein in an initial, biological sample is generally designated by the reference numeral 240. Device 240 is similar in structure to device 10, and as such, the prior description of device 10 is understood to describe device 240 except as herein provided.

Figure 9A:
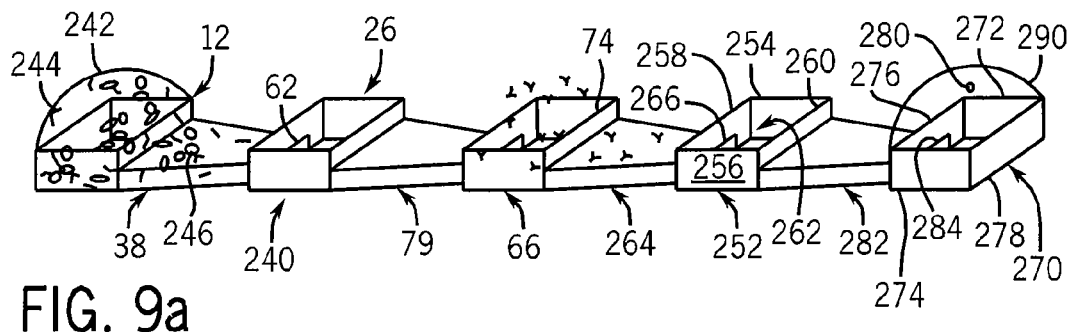
FIGS. 9a-9e are schematic, isometric views of a still further embodiment of a device in accordance with the present invention wherein a series of operational steps associated with quantifying a level of a specific particle/protein in an initial sample is depicted.
Figure 9B:
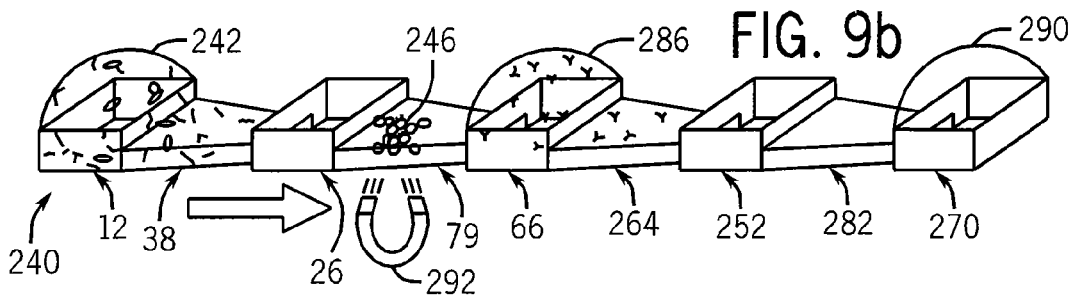

As best seen in FIG. 9a, device 240 includes a second phase-gate zone or well 252 downstream of output well 66 and being defined by first and second sidewalls 254 and 256, respectively, upstream wall 258, and downstream wall 260. The inner surfaces of sidewalls 254 and 256, respectively, the inner surface of upstream wall 258, and the inner surface of downstream wall 260 define a phase-gate cavity 262 for receiving an isolation buffer therein, as heretofore described.

Again, although phase-gate well 252 has a generally rectangular configuration in the depicted embodiment, other configurations are contemplated without deviating from the scope of the present invention.

Output well 66 and second phase-gate well 252 are interconnected by third channel 264. Third channel 264 extends along an axis and is defined by first and second sidewalls, an upper wall and a bottom wall. The input ends of the first and second sidewalls of third channel 264 and the input end of the upper wall of third channel 264 intersect end wall 74 of output well 66 so as to define an input to third channel 264. The output ends of the first and second sidewalls of third channel 264 and the output end of the upper wall of third channel 264 intersect upstream wall 258 of phase-gate well 252 so as to define output 266 of third channel 264. The bottom wall of third channel 264 is generally co-planar with bottom walls 22 and 36 of input well 12 and phase-gate well 26, respectively. It can be seen that the first and second sidewalls of third channel 264 converge towards each other from the input to output 266 thereof, for reasons hereinafter described.

Device 240 further includes a second output zone or well 270 downstream of second phase-gate well 252 and being defined by first and second sidewalls 272 and 274, respectively, upstream wall 276, and downstream wall 278. The inner surfaces of first and second sidewalls 272 and 274, respectively, the inner surface of upstream wall 276, and the inner surface of downstream wall 278 define output cavity 280 for receiving a reagent therein, as hereinafter described. Again, second output well 270 has a generally rectangular configuration in the depicted embodiment, other configurations are contemplated without deviating from the scope of the present invention.

Second output well 270 and second phase-gate well 252 are interconnected by fourth channel 282. Fourth channel 282 extends along an axis and is defined by first and second sidewalls, an upper wall and bottom wall. The input ends of the first and second sidewalls of fourth channel 282 and the input end of the upper wall of fourth channel 282 intersect downstream wall 260 of second phase-gate well 252 so as to define an input to fourth channel 282. The output ends of the first and second sidewalls of fourth channel 282 and the output end of the upper wall of fourth channel 282 intersect upstream wall 276 of second output well 270 so as to define output 284 of fourth channel 282. The bottom wall of fourth channel 282 is generally co-planar with bottom walls second of phase-gate well 252 and output well 66, respectively. It can appreciated the first and second sidewalls of fourth channel converge towards each other from the input to the output, for reasons hereinafter described.

In operation, a biological sample 242 is provided. As is known, biological sample 242 may include a protein of interest, along with non-desired material 244 such as lysate, bodily fluids, forensic samples, and/or biological contaminations. In order to prepare biological sample 242, biological sample 242 is mixed with a solid phase substrate, such as antibody-coated, paramagnetic particles, such that the desired protein binds to the antibody-coated, paramagnetic particles to form protein-bound paramagnetic particles 246. It is contemplated for the protein-bound paramagnetic particles 246 to be attracted to a corresponding magnetic field. Thereafter, biological sample 242 is allowed to incubate for a predetermined time period (e.g. 1 hour) and deposited in input cavity 24 of input well 12; isolation buffer 109, such as oil or wax, is deposited in phase-gate cavity 37 of phase-gate well 26; labeling buffer 286, hereinafter described, is deposited in output cavity 78 of output well 66; an isolation buffer, such as oil or wax, is deposited in second phase-gate cavity 262 of phase-gate well 252; and a readout buffer 290, hereinafter described, deposited in output cavity 280 of second output well 270, FIG. 9a. It is contemplated for labeling buffer 286 to include an additional antibody which either contains or can be later functionalized with a detectable molecule (e.g. fluorescent protein, HRP enzyme or the like). Readout buffer 290 contains material which is conducive to quantifying the amount of protein through some optical measurement (e.g. fluorescence, chemiluminescence, metabolism of a substrate to produce a colored metabolite).

As heretofore described, it is contemplated for the solid phase substrate to be a paramagnetic material attracted to a corresponding magnetic field. As such, in order to generate the magnetic field, magnet 292 is positioned below input well 12 such that protein-bound paramagnetic particles 246 are magnetically attracted thereto. Magnet 292 is sequentially moved: 1) below bottom wall 45 of first channel 38 such that protein-bound paramagnetic particles 246 are drawn into first channel 38 through input 52 thereof; 2) below bottom wall 36 of phase-gate well 26 such that protein-bound paramagnetic particles 246 are drawn into phase-gate well 26 through output 62 of first channel 38; 3) below bottom wall 85 of second channel 79 such that protein-bound paramagnetic particles 246 are drawn into second channel 79 through input 92 thereof, FIG. 9b; and 4) below bottom wall 76 of output well 66 such that protein-bound paramagnetic particles 246 are drawn into output well 66 through output 102 of second channel, FIG. 9c.

As previously noted, the surface tension of isolation buffer 109 in phase-gate cavity 37 of phase-gate well 26 at output 62 of first channel 38 prevents biological sample 242 from flowing into phase-gate cavity 37 of phase-gate well 26 through output 62 of first channel 38 and the surface tension of labeling buffer 286 in output cavity 78 of output well 66 at output 102 of second channel 79 prevents isolation buffer 109 from flowing into output cavity 78 of output well 66 at output 102 of second channel 79. It can be appreciated that as protein-bound paramagnetic particles 246 pass through phase-gate well 26 and second channel 79, protein-bound paramagnetic particles 246 are washed by isolation buffer 109 therein, thereby effectively isolating protein-bound paramagnetic particles 246 from the remainder of biological sample 242. With protein-bound paramagnetic particles 246 isolated from the remainder of biological sample 242 in output well 66, protein-bound paramagnetic particles 246 in output well 66 are labeled by protein-bound paramagnetic particles 246 in the labeling buffer 286.

Figure 9C:
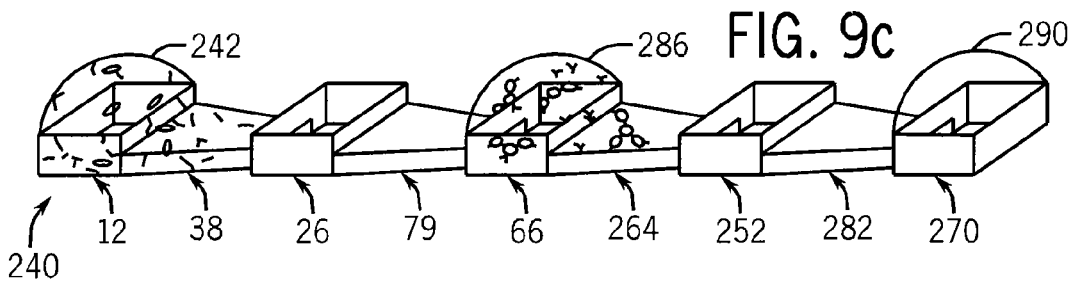
Figure 9D:
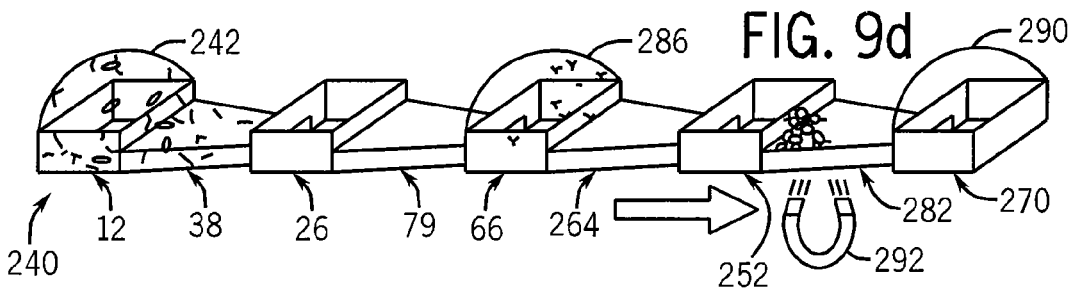
Figure 9E:
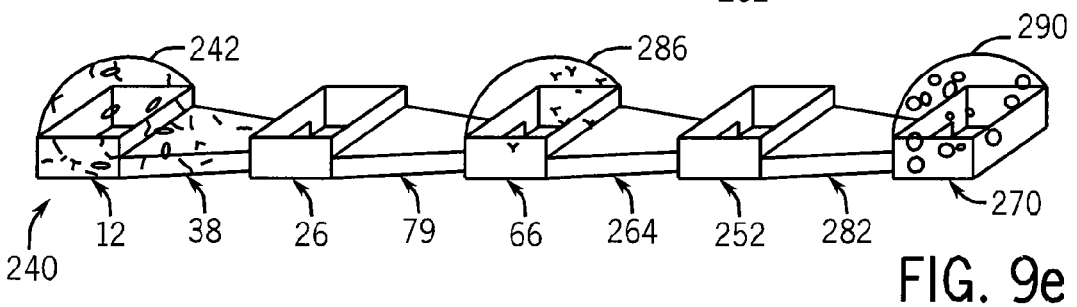
Figure 10A:
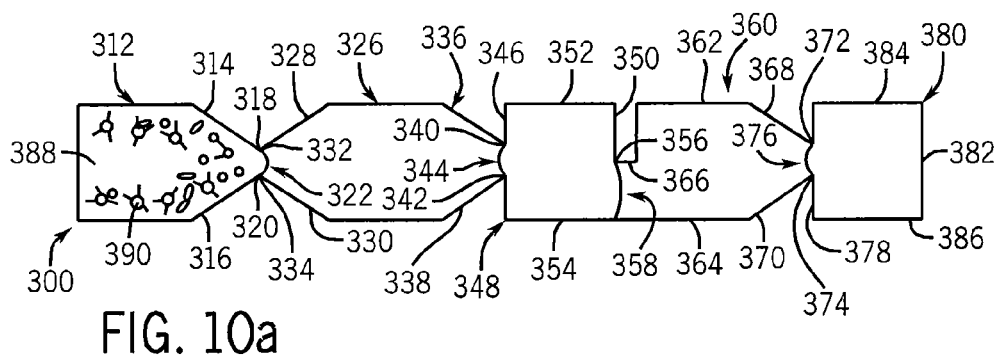
FIGS. 10a-10d are schematic, isometric views of a platform incorporating the device of the present invention wherein a series of operational steps associated with extracting a quantity of specific particles/proteins from an initial sample and splitting the quantity of extracted particles/proteins into subsets is depicted.
Figure 10B:
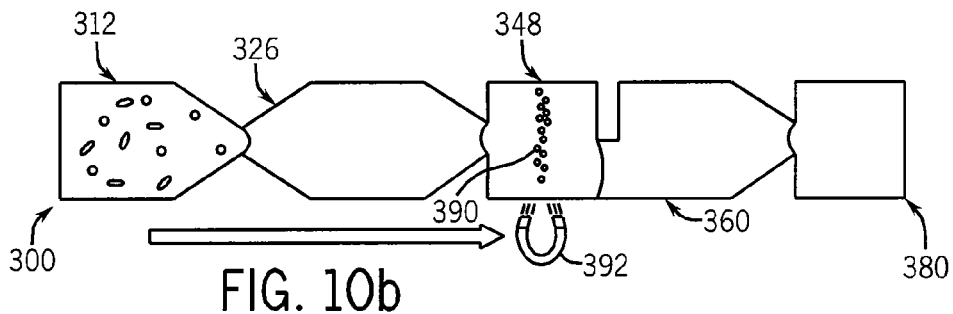
Figure 10C:
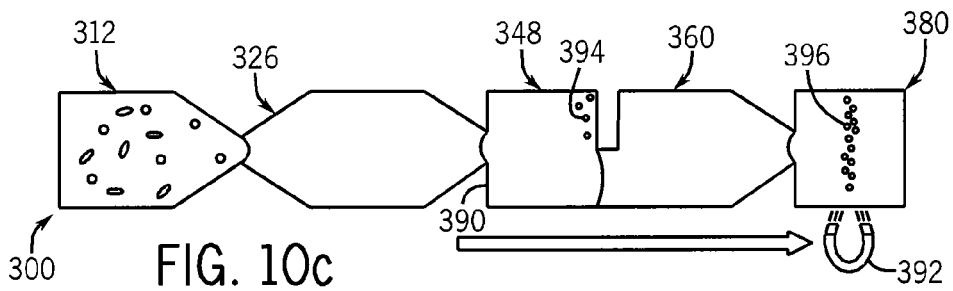
Figure 10D:
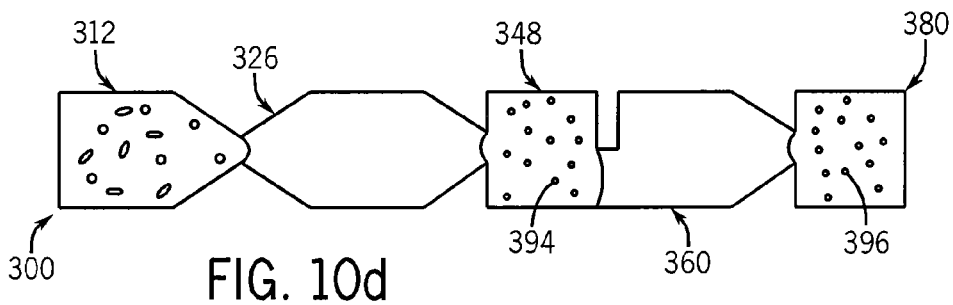

After a predetermined time period for allowing the antibody in the labeling buffer 286 to bind to protein-bound paramagnetic particles 246, FIG. 9c, magnet 292 is sequentially moved: 1) below the bottom wall of third channel 264 such that labeled protein-bound paramagnetic particles 246 are drawn into third channel 264; 2) below the bottom wall of second phase-gate well 252 such that labeled protein-bound paramagnetic particles 246 are drawn into second phase-gate well 252 through the output of third channel 264; 3) below the bottom wall of fourth channel 282 such that labeled protein-bound paramagnetic particles 246 are drawn into fourth channel 282 through the input thereof, FIG. 9d; and 4) below the bottom wall of second output well 270 such that label protein-bound paramagnetic particles 246 are drawn into second output well through output 284 of fourth channel 282, FIG. 9e.

As previously noted, the surface tension of the isolation buffer in second phase-gate cavity 262 of second phase-gate well 252 at output 266 of third channel 264 prevents unbound detectable antibodies from flowing into second phase-gate cavity 262 of phase-gate well 252 through output 266 of third channel 264 and the surface tension of readout buffer 290 in output cavity 280 of second output well 270 at output 284 of fourth channel 282 prevents the isolation buffer from flowing into output cavity 280 of second output well 270 at output 284 of fourth channel 282. It can be appreciated that as labeled protein-bound paramagnetic particles 246 pass through second phase-gate well 252 and fourth channel 282, labeled protein-bound paramagnetic particles 246 are washed by the isolation buffer therein, thereby effectively isolating labeled protein-bound paramagnetic particles 246 from the unbound antibodies. With labeled protein-bound paramagnetic particles 246 isolated from the unbound antibodies in second output well 270, labeled protein-bound paramagnetic particles 246 in second output well 270 may be quantified to determine the level of desired protein in biological sample 242.

As described, device 240 simplifies the enzyme-linked immunosorbant assay (ELISA) by utilizing immiscible phase barriers to eliminate time-consuming washing steps. Conventional ELISA relies upon multiple washing steps to isolate unbound proteins and bulk lysate from the desired protein-of-interest. An additional set of washing steps is also needed to remove unbound detectable antibodies from the assay to prevent a false positive signal. These washing steps, often six (6) or more in total, are time consuming as liquids are often added, mixed and removed manually. Additionally, the washing steps promote unwanted dissociation of the protein-of-interest from the capture resin due either to the fluidic shear stress generated during washing (weakly captured proteins) and/or the added time required for washing (short complex half-life).

Referring to FIGS. 10a-10d, a device for partitioning purified nucleic acid (NA) into multiple wells is generally designated by the reference numeral 300. Device 300 includes input zone or well 312 partially defined by upper and lower converging walls 314 and 316, respectively, having terminal ends 318 and 320, respectively, defining an output 322 of input well 312. It is intended for input well 312 to receive a biological sample therein, for reasons hereinafter described.

Device 300 further includes first phase-gate zone or well 326 downstream of input well 312. First phase-gate well 326 is partially defined upper and lower diverging input walls 328 and 330, respectively, having input ends 332 and 334, respectively, intersecting terminal ends 318 and 320, respectively, of upper and lower converging walls 314 and 316, respectively. First phase-gate well 326 is further defined upper and lower converging output walls 336 and 338, respectively, having output ends 340 and 342, respectively, defining output 344 of first phase-gate well 326. Output 344 of first phase-gate well 326 is centrally located on upstream wall 346 of first reaction well 348. First reaction well 348 is further defined by downstream wall 350, upper wall 352 and lower wall 354. Terminal end 356 of downstream wall 350 and lower wall 354 define output 358 of first reaction well 348. It is intended for downstream wall 350 to be approximately one-half the length of upstream wall 346, for reasons hereinafter described.

Device 300 further includes second phase-gate zone or well 360 downstream of first reaction well 348. Second phase-gate well 360 is partially defined upper and lower, generally parallel input walls 362 and 364, respectively. Input end 366 of upper input wall 362 intersects terminal end 356 of downstream wall 350 of first reaction well 348. Lower input wall 364 of second phase-gate well 360 intersects and is generally co-planar to lower wall 354 of first reaction well 348. Second phase-gate well 360 is further defined by upper and lower converging output walls 368 and 370, respectively, having output ends 372 and 374, respectively, defining output 376 of second phase-gate well 360. Output 376 of second phase-gate well 360 is centrally located on upstream wall 378 of second reaction well 380. Second reaction well 380 is further defined by downstream wall 382, upper wall 384 and lower wall 386.

In operation, biological sample 388 is mixed with a solid phase substrate, e.g. silica or oligo(dT)-coated, paramagnetic particles, such that the desired NA bind to the coated, paramagnetic particles to form NA-bound paramagnetic particles 390. It is contemplated for the NA-bound paramagnetic particles 390 to be attracted to a corresponding magnetic field. Thereafter, biological sample 388 is allowed to incubate for a predetermined time period (e.g. 1 hour) and deposited in input well 312; an isolation buffer, such as oil or wax, is deposited in first phase-gate well 326; a first multi-color, one-step RT-PCR reagent is loaded into first reaction well 348; an isolation buffer, such as oil or wax, is deposited in second phase-gate well 360; and a second multi-color, one-step RT-PCR reagent is loaded into second reaction well 380. It is intended for the first and second multi-color, one-step RT-PCR reagents to amplify two sets of genes (one set per reaction well) in parallel, as hereinafter described.

Once device 300 is loaded, as heretofore described, magnet 392 is positioned below input well 312 such that mRNA-bound paramagnetic particles 390 are magnetically attracted thereto. It is noted that the paramagnetic particles attracted to a magnet, e.g. magnet 392, extend linearly away from the edge of the magnet, FIG. 10b and that paramagnetic particles are easily trapped against walls or obstacles placed in their path, FIG. 10c. Magnet 392 is sequentially moved 1) below the bottom wall of first phase-gate well 326 such that NA-bound paramagnetic particles 390 are drawn therein; and 2) below first reaction well 346 such that NA-bound paramagnetic particles 390 are drawn therein. As previously noted, the surface tension of the isolation buffer in first phase-gate well 326 at output 322 of input well 312 prevents biological sample 388 from flowing into first phase-gate well 326. Thereafter, magnet 392 is sequentially moved 1) below lower wall 364 of second phase-gate well 360 such that first portion 394 of NA-bound paramagnetic particles 390 engage downstream wall 350 of first reaction well 346 and are maintained within first reaction well 348 and such that second portion 396 of NA-bound paramagnetic particles 390 are drawn into second phase-gate well 360 through output 358 of first reaction well 348; and 2) below second reaction well 380 such that second portion 396 of NA-bound paramagnetic particles 390 are drawn into second reaction well 380 through output 376 of second phase-gate well 360.

Given that paramagnetic particles are easily trapped against walls or obstacles placed in their path, it can be appreciated that device 300 allows a user to simply and easily split NA-bound paramagnetic particles 390 into first and second generally equal portions 394 and 396, respectively. As a result, with first and second reaction wells 348 and 380, respectively, preloaded with multi-color, one-step RT-PCR reagents, a user may amplify two sets of genes (one set per reaction well) simultaneously. In order to standardize first and second portions 394 and 396, respectively, of NA-bound paramagnetic particles 390, it is contemplated to analyze a common gene from each reaction well 348 and 380 to measure the relative quantity of mRNA distributed thereto. It can be appreciated that device 300 may be further expanded to allow for the analysis of additional genes by introducing more stages (phase-gate well and reaction well combinations) into the design.

Heretofore, the various channels between the wells of the devices have been described as having generally trapezoidal cross-sections. The trapezoidal configuration of the channels is intended to minimize the interface between each phase\fluid such that surface energy forces dominate gravitational forces at such interfaces, thereby stabilizing the side-by-side positioning of the phases\fluids. Alternatively, the wells may be separated, not by trapezoidal-shaped channels, but by vertical partitions which create a constriction in the Z direction rather than in the Y direction. More specifically, referring to FIGS. 12-13, an alternate embodiment of a device for extracting and purifying a fraction from cultured cells, tissue samples and other biological materials in accordance with the present invention is generally designated by the reference numeral 400. Device 400 includes input zone or well 412 defined by first and second sidewalls 414 and 416, respectively, upstream wall 418, downstream wall 420, respectively, and bottom wall 422. Downstream wall 420 extends away from upstream wall 418 and has a terminal end 424 spaced from bottom wall 422 so as to define output 421. The inner surfaces 414a and 416a of sidewalls 414 and 416, respectively, inner surfaces 418a and 420a of upstream and downstream walls 418 and 420, respectively, and upper surface 422a of bottom wall 422 define input cavity 425 for receiving a biological sample therein, as hereinafter described. While input well 412 has a generally rectangular configuration in the depicted embodiment, other configurations are contemplated without deviating from the scope of the present invention.

Device 400 further includes phase-gate zone or well 426 downstream of input well 412 and being defined by first and second sidewalls 428 and 430, respectively, upstream wall 432, downstream wall 434 and bottom wall 436. Upstream wall 432 and downstream wall 434 of phase-gate well 426 diverge from each other and have corresponding terminal ends 438 and 440 spaced from bottom wall 436. Terminal end 438 of upstream wall 432 of phase-gate well 426 intersects terminal end 424 of downstream wall 420 of input well 412. Terminal end 440 of downstream wall 434 of phase-gate well 426 and bottom wall 436 are spaced so as to define output 441. Inner surfaces 428a and 430a of sidewalls 428 and 430, respectively, inner surface 432a of upstream wall 432, inner surface 434a of downstream wall 434 and upper surface 436a of bottom wall 436 define phase-gate cavity 437 for receiving an isolation buffer therein, as hereinafter described. Again, although phase-gate well 426 has a generally rectangular configuration in the depicted embodiment, other configurations are contemplated without deviating from the scope of the present invention.

Device 400 further includes output zone or well 466 downstream of phase-gate well 426 and being defined by first and second sidewalls 468 and 470, respectively, upstream wall 472, downstream wall 474 and bottom wall 476. Upstream wall 472 extends away from downstream wall 474 of output well 466 and has a terminal end 480 spaced from bottom wall 476. Terminal end 480 of upstream wall 472 of output well 466 intersects terminal end 440 of downstream wall 434 of phase-gate well 426. Inner surfaces 468a and 470a of sidewalls 468 and 470, respectively, inner surface 472a of upstream wall 472, inner surface 474a of downstream wall 474, and upper surface 476a of bottom wall 476 define output cavity 478 for receiving a reagent therein, as hereinafter described. Again, output well 466 has a generally rectangular configuration in the depicted embodiment, other configurations are contemplated without deviating from the scope of the present invention.

In operation, an appropriate reagent is added to biological sample 106 and mixed such that fraction 104 binds to a solid phase substrate in the reagent to form fraction-bound solid phase substrate 110, as heretofore described. Once mixed with the reagent, biological sample 106 is deposited in input cavity 424 of input well 412; an isolation buffer, such as oil or wax, is deposited in phase-gate cavity 437 of phase-gate well 426; and a desired reagent is deposited in output cavity 478 of output well 466. It can be appreciated that the mixing of biological sample 106 and the reagent may occur in input cavity 424 of input well 412 without deviating from the scope of the present invention.

It is noted that the surface tension of isolation buffer in phase-gate cavity 437 of phase-gate well 426 at output 441 of input well 412 prevents biological sample 106 from flowing into phase-gate cavity 437 of phase-gate well 426 therethrough. Likewise, the surface tension of the reagent in output cavity 478 of output well 466 at output 441 of phase-gate well 426 prevents the isolation buffer in phase-gate well 426 from flowing into output cavity 478 of output well 466 therethrough.

In order to extract fraction-bound solid phase substrate 110 from biological sample 106, a force to which the solid phase substrate is attracted is positioned adjacent, and preferably below, input well 412. As heretofore described, it is contemplated for the solid phase substrate to be a paramagnetic material attracted to a corresponding magnetic field. As such, in order to generate the magnetic field, a magnet is positioned below input well 412 such that fraction-bound solid phase substrate 110 is magnetically attracted thereto. Magnet 111 is sequentially moved: 1) below bottom wall 436 of phase-gate well 426 such that fraction-bound solid phase substrate 110 are drawn into phase-gate well 426 through output 421 of input well 412; and 2) below bottom wall 476 of output well 466 such that fraction-bound solid phase substrate 110 are drawn into output well 466 through output 441 of phase-gate well 426.

It can be appreciated that as fraction-bound solid phase substrate 110 passes through phase-gate well 426, fraction-bound solid phase substrate 110 are washed by the isolation buffer therein, thereby effectively isolating fraction-bound solid phase substrate 110 from the remainder of biological sample 106. With fraction-bound solid phase substrate 110 isolated from the remainder of biological sample 106 in output well 466, fraction-bound solid phase substrate 110 may be treated in output well 466 by the reagent contained therein as desired by a user. In addition, it can be appreciated that output well 466 may be operatively connected to additional downstream components for further processing of fraction-bound solid phase substrate 110.

As described, device 400 provides certain advantages over the alternate embodiments of the present invention. More specifically, by providing constrictions in the Z axis direction instead of the Y axis direction, the fraction-bound solid phase substrate 110 may be spread across the entire width of device 400 as the phase interface width is not constrained. This is particularly advantageous when using high fraction-bound solid phase substrate concentrations or in cases where the fraction-of-interest is very large (e.g. whole cells), as the aggregate may clog a constrained interface width. Further, by eliminating the channels in device 400, the likelihood of air being trapped within the device is dramatically reduced, thereby resulting in more predictable permeability between the phase\fluid interfaces.

It is also noted that it contemplated as being within the scope of the present invention to provide an array of the devices as heretofore described in combination with an array of permanent magnets in a 1:1 ratio. Alternatively, an array of electromagnets may be utilized to provide adaptable and programmable movement of the magnetic field with no moving parts. Also, bar magnets may that simultaneously move the solid phases through multiple independent phase gates may be use. It can be appreciated that in all permanent magnet embodiments of the present invention, either the magnet or the device of the present invention can be the movable part. Additionally, in all embodiments, physical alignment constructs ensure precise alignment between the device of the present invention and the magnetic apparatus.

Figure 16:
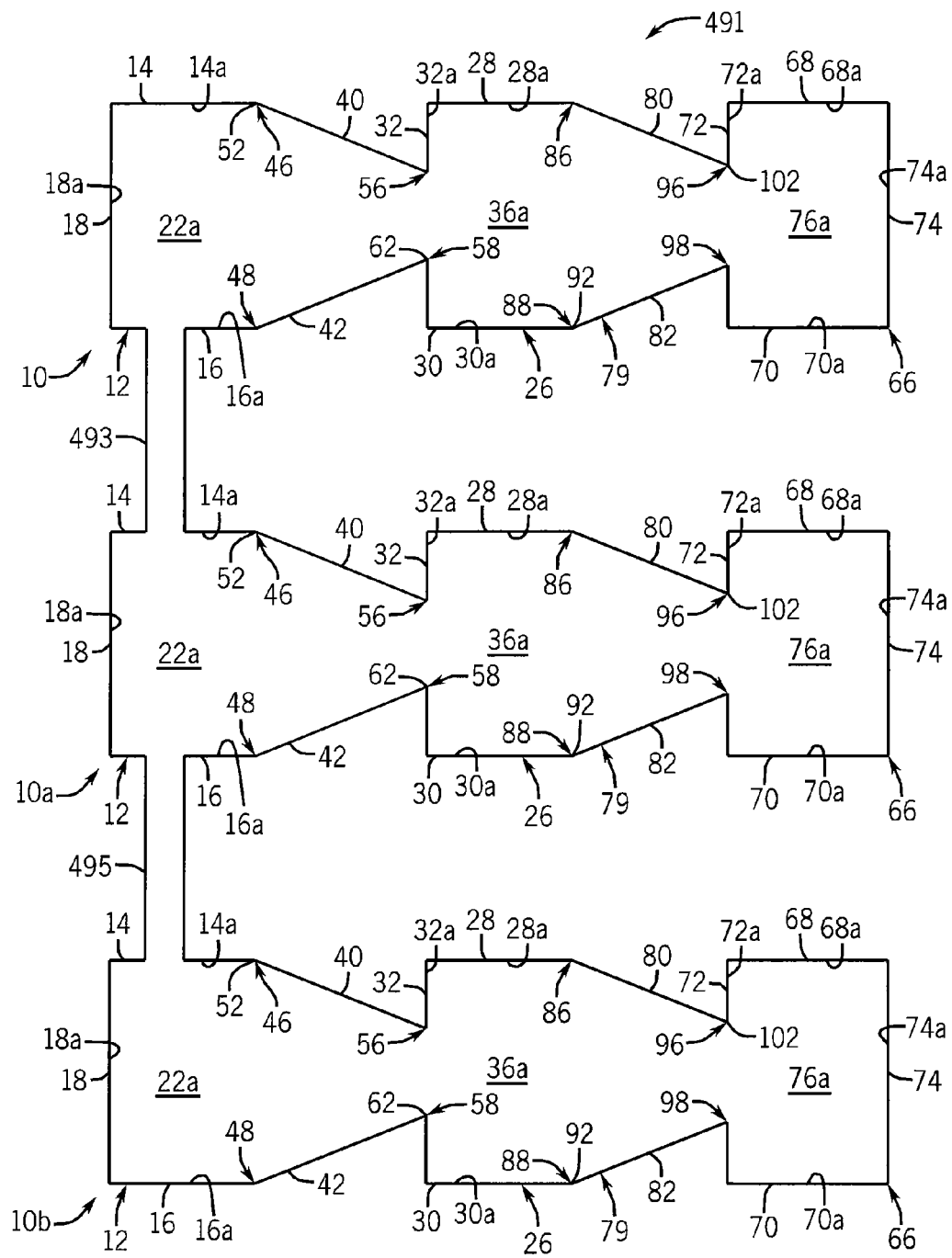
FIG. 16 is a top plan view of an array of the device of FIG. 1 wherein the input wells of the devices are interconnected.

Referring to FIG. 16, it is contemplated to interconnect selected wells of adjacent devices of the present invention arranged in an array, generally designated by the reference numeral 491, for reasons hereinafter described. By way of example, array 491 may include a plurality of devices 10, 10a and 10b. Devices 10, 10a and 10b are identical in structure, and as such, the previous description of device 10 is understood to describe devices 10a and 10b as if fully described herein. It can be appreciated that the number of devices in array 491 and/or the type of devices may vary without deviating from the scope of the present invention.

In the depicted embodiment, input cavity 24 of input well 12 of device 10 is interconnected to input cavity 24 of input well 12 of device 10a by first connection channel 493. Similarly, input cavity 24 of input well 12 of device 10a is interconnected to input cavity 24 of input well 12 of device 10b by second connection channel 495. By interconnecting input wells 12 of devices 10, 10a and 10b, a common sample may be simply and easily loaded into the input wells 12 and processed by devices 10, 10a and 10b, as desired by a user.

Figure 17:
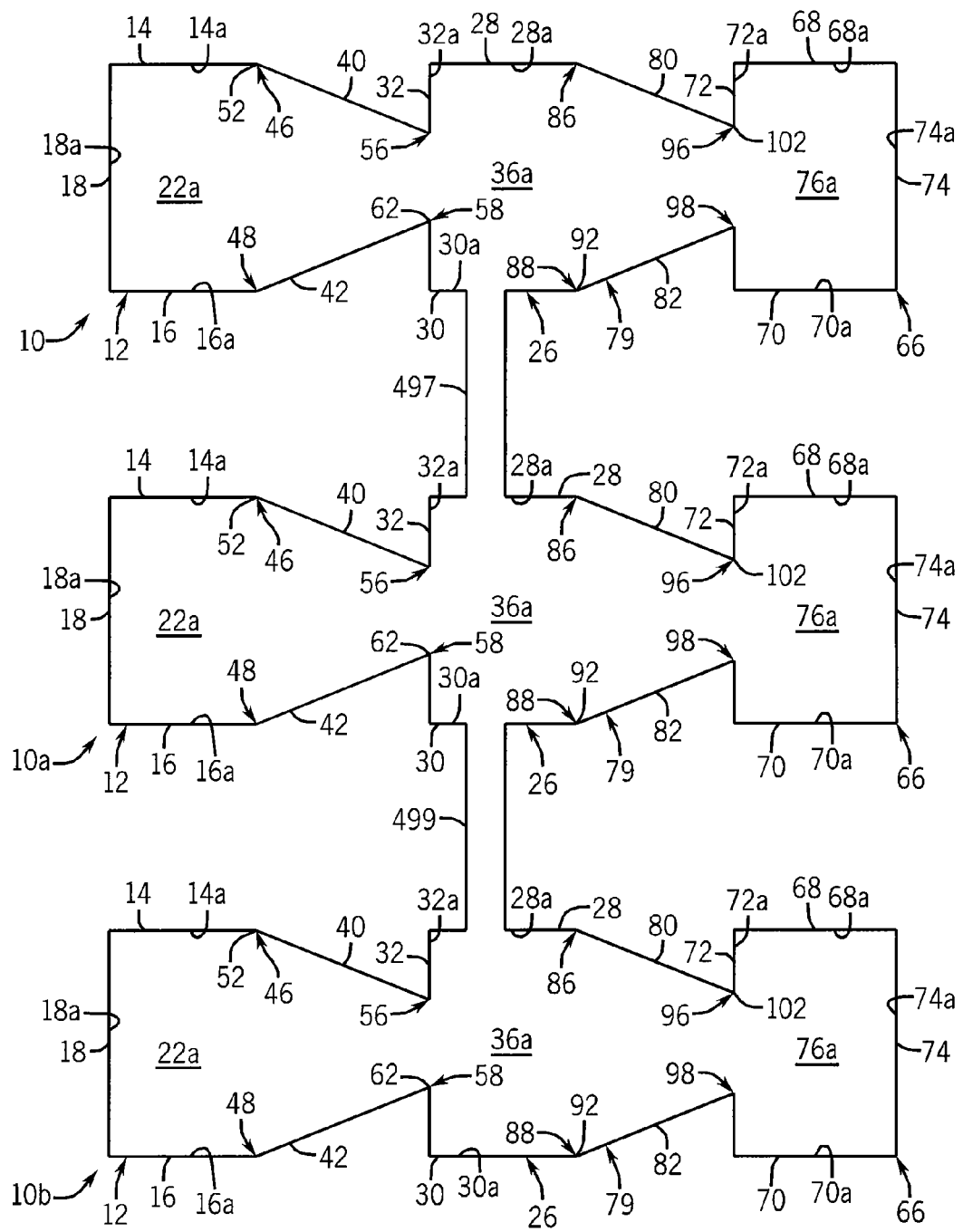
FIG. 17 is a top plan view of an array of the device of FIG. 1, similar to FIG. 16, wherein the phase-gate wells of the devices are interconnected.

Referring to FIG. 17, in an alternate embodiment, phase-gate cavity 37 of phase-gate well 26 of device 10 is interconnected to phase-gate cavity 37 of phase-gate well 26 of device 10a by first connection channel 497. Similarly, phase-gate cavity 37 of phase-gate well 26 of device 10a is interconnected to phase-gate cavity 37 of phase-gate well 26 of device 10b by second connection channel 499. By interconnecting phase-gate wells 26 of devices 10, 10a and 10b, a common isolation fluid may be simply and easily loaded into phase-gate wells 26 in devices 10, 10a and 10b. It is understood that other wells herein described (e.g., wash wells, output wells, etc.) may be interconnected to facilitate loading of devices 10, 10a and 10b and/or processing of a fraction of a biological sample.

Figure 14:
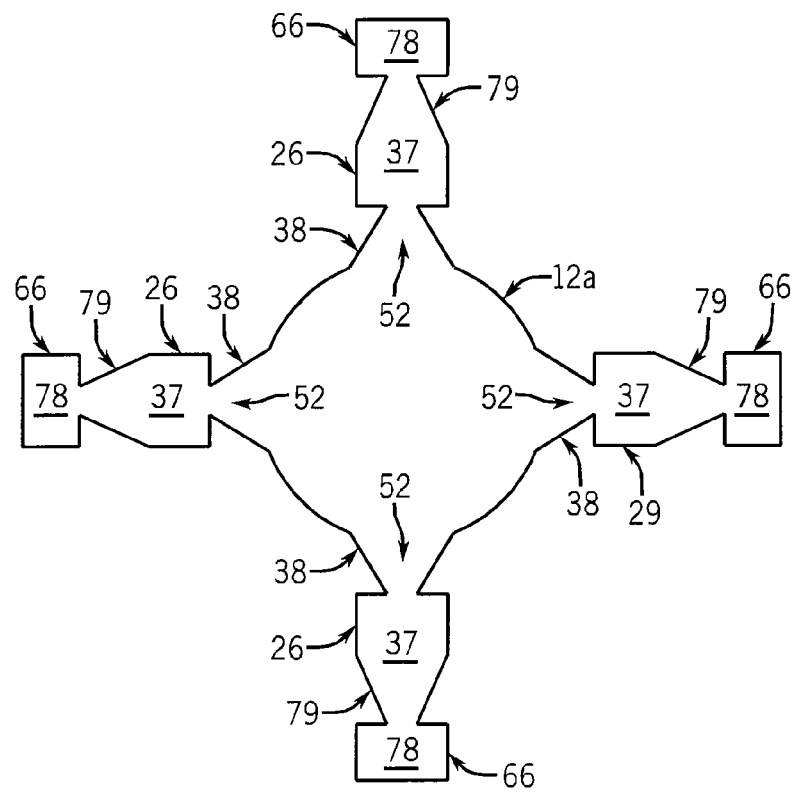
FIG. 14 is a top plan view of a still further embodiment of a device in accordance with the present invention.

Referring to FIG. 14, it is contemplated for the device of the present invention to incorporate a central input well having a plurality of phase-gate well and output well combinations projecting radially therefrom. More specifically, input well 12 of device 10 is replaced by central input well 12a having a generally circular configuration. However, other configurations for input well 12a are contemplated as being within the scope of the present invention. Inputs 52 to a plurality of circumferentially spaced, first channels 38 communicate with central input well 12a.

In operation, as heretofore described, an appropriate reagent is added to biological sample 106 and mixed such that fraction 104 binds to a solid phase substrate in the reagent to form fraction-bound solid phase substrate 110. Once mixed with the reagent, biological sample 106 is deposited within input well 12a; an isolation buffer, such as oil or wax, is deposited in phase-gate cavities 37 of phase-gate well 26; and a desired reagent is or reagents are deposited in output cavities 78 of output wells 66. It can be appreciated that the mixing of biological sample 106 and the reagent may occur within input well 12a and/or first channels 38 without deviating from the scope of the present invention.

In order to extract fraction-bound solid phase substrate 110 from biological sample 106, a force to which the solid phase substrate is attracted is positioned adjacent, and preferably below, input well 12a. As heretofore described, it is contemplated for the solid phase substrate to be a paramagnetic material attracted to a corresponding magnetic field. As such, in order to generate the magnetic field, a plurality of magnets corresponding in number to the number of inputs 52 to first channels 38 (e.g. four (4) in the depicted embodiment) are positioned below input well 12a such that portions of fraction-bound solid phase substrate 110 are magnetically attracted thereto. The magnets are moved radilly outward such that each magnet is sequentially moved: 1) below bottom wall 45 of a corresponding first channel 38 such that a portion of fraction-bound solid phase substrate 110 is drawn into the corresponding first channel 38 through input 52 thereof; 2) below bottom wall 36 of a corresponding phase-gate well 26 such that the portion of the fraction-bound solid phase substrate 110 is drawn into the corresponding phase-gate well 26 through output 62 of the corresponding first channel 38; 3) below bottom wall 85 of a corresponding second channel 79 such that the portion of fraction-bound solid phase substrate 110 is drawn into the corresponding second channel 79 through input 92 thereof; and 4) below bottom wall 76 of a corresponding output well 66 such that the portion of fraction-bound solid phase substrate 110 is drawn into the corresponding output well 66 through output 102 of the corresponding second channel 79.

With portions of fraction-bound solid phase substrate 110 isolated from the remainder of biological sample 106 and from each other in corresponding output wells 66, the portions of fraction-bound solid phase substrate 110 may be treated in output wells 66 by single common reagent or by different reagents in the output wells 66 contained therein as desired by a user. In addition, it can be appreciated that output wells 66 may be operatively connected to additional downstream components, as heretofore described, for further processing of the portions of fraction-bound solid phase substrate 110.

Figure 15:
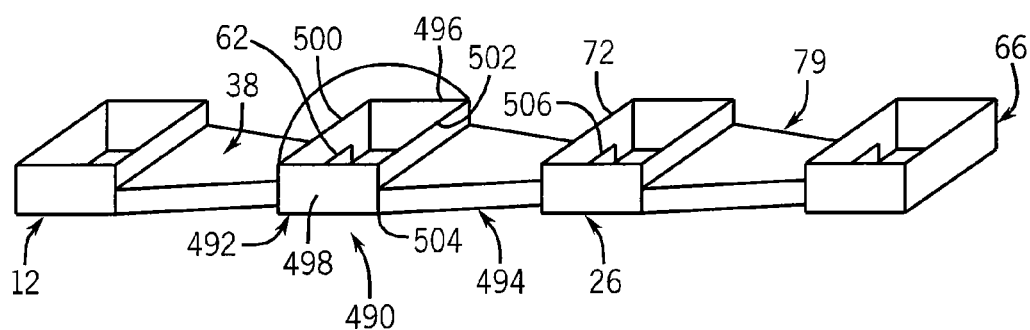
FIG. 15 is an isometric view of the device of FIG. 1 incorporating an immobilized liquid plug to facilitate loading of the device.

Referring to FIG. 15, it is further contemplated to provide an immobilized fluid plug structure, generally designated by the reference numeral 490, between first channel 38 and phase-gate well 26, as hereinafter described. It is intended for immobilized fluid plug structure 490 to physically separate first channel 38, and hence input well 12, from phase-gate well 26, so as to prevent the exchange of fluids therebetween. More specifically, it is noted that in the case of nucleic acid and protein purification, the reagent added to biological sample 106 will likely include a lysis buffer, which typically has a high concentration (0.5% to 2% or more) of one or more detergents (e.g. NP-40, SDS, LiDS, Triton X-100, Tween 20). As the inclusion of detergent significantly reduces the surface tension of a fluid, the inclusion of these lysis buffers in the reagent could potentially impact the filling of device 10 which relies upon surface tension to position each reagent within corresponding wells.

Plug structure 490 includes immobilized fluid plug well 492 and plug channel 494 extending therefrom. Plug well 492 is downstream of input well 12 and is defined by first and second sidewalls 496 and 498, respectively, upstream wall 500, downstream wall 502 and bottom wall 504. The inner surfaces sidewalls 496 and 498, respectively, the inner surface of upstream wall 500, the inner surface of downstream wall 502, and upper surface of bottom wall 504 define a plug cavity for receiving a plug fluid therein. Output 62 of first channel 38 is provided in upstream wall 500 so as to allow the plug cavity to communicate therewith. For reasons hereinafter described, the plug fluid is an aqueous solution having a high surface tension (e.g., water or phosphate buffered saline). Although plug well 492 has a generally rectangular configuration in the depicted embodiment, other configurations are contemplated without deviating from the scope of the present invention.

Plug channel 494 extends along an axis and is defined by first and second sidewalls, an upper wall and a bottom wall. The input ends of the first and second sidewalls of plug channel 494 and the input end of the upper wall of plug channel 494 intersect downstream wall 502 of plug well 492 so as to define an input to plug channel 494. The output ends of the first and second sidewalls of plug channel 494 and the output end of the upper wall of plug channel 494 intersect upstream wall 72 of output well 66 so as to define output 506 of plug channel 494. The bottom wall of plug channel 494 is generally co-planar with bottom walls 36 and 76 of phase-gate well 26 and output well 66, respectively. It can be appreciated that the first and second sidewalls of plug channel 494 converge towards each other from the input to the output, for reasons heretofore described.

During the loading of device 10, as heretofore described, it is intended to load immobilized liquid plug well 492 with an aqueous solution having a high surface tension. The aqueous solution will physically separates the isolation fluid in phase-gate well 26 from the reagent in input well 12, thereby eliminating the possibility of leakage. It is contemplated for the aqueous solution to be any fluid with reasonably high surface tension (>10 mN/m) that will not adversely affect the lysate in biological sample 106 upon contact. Further, it can be appreciated the aqueous solution and the lysate in biological sample 106 (which is also aqueous in most cases) will mix with the aqueous solution upon contact due to the miscibility of these two fluids. While this will result in the dilution of the lysate, the final purified analyte concentration will be unchanged from the initial embodiment since the final well volume and analyte binding capacity of the solid phase substrate remain unchanged. Furthermore, the volume of plug well 492 can be significantly smaller (e.g., 25-fold smaller) than the volume of biological sample 106 in input well 12, resulting in minimal changes to lysate concentration/volume. Once device 10 is loaded, fraction-bound solid phase substrate 110 may be extracted from biological sample 106 as heretofore described.

Various modes of carrying out the invention are contemplated as being within the scope of the following claims particularly pointing out and distinctly claiming the subject matter, which is regarded as the invention.

We claim:

1. A device for facilitating extraction of a fraction from a biological sample, the biological sample including a fraction, non-desired material and a solid phase substrate, the device comprising:
   an input zone for receiving the biological sample therein, the fraction binding to the solid phase substrate to form a fraction-bound solid phase substrate;
   a phase-gate zone communicating with the input zone and receiving an isolation buffer therein;
   an elution zone communicating with the phase-gate zone and receiving a reagent therein, the reagent extracting the fraction from the fraction-bound solid phase substrate;
   a wash zone having an input communicating with the elution zone and an output communicating with the input zone, the wash zone receiving a wash buffer therein for regenerating the solid phase substrate; and
   a force movable between a first position adjacent the input zone, a second position adjacent the phase-gate zone, a third position adjacent the elution zone, and a fourth position adjacent the wash zone;
   wherein the force sequentially moves:
   from the first position to the second position so as to urge the fraction-bound solid phase substrate from the input zone to the phase-gate zone;
   from the second position to the third position so as to urge the fraction-bound solid phase substrate from the phase-gate zone to the elution zone wherein the fraction is extracted from the fraction-bound solid phase substrate such that solid phase substrate remains;
   from the third position to the fourth position so as to urge the solid phase substrate from the elution zone to the wash zone wherein the solid phase substrate is regenerated; and
   from the fourth position to the first position so as to urge the solid phase substrate from the wash zone to the input zone wherein the solid phase substrate is free to bind with an additional fraction.

2. The device of claim 1 further comprising an isolation buffer received in the phase-gate zone and wherein the isolation buffer is an oil, the oil preventing the non-desired material from passing therethrough.

3. A platform for isolating biomolecules from cell cultures, the platform comprising:
   a channel having an input and an output, the channel adapted for receiving a cell culture therein;
   a solid phase substrate in the channel, a biomolecule binding to the solid phase substrate to form a biomolecule-bound solid phase substrate;
   a phase-gate zone having an input communicating with the channel, the phase-gate zone receiving an isolation buffer therein;
   an output zone for receiving a reagent therein;
   a force movable between a first position adjacent the channel and a second position adjacent the output zone;
   a second channel having an input and an output, the second channel communicating with the first channel and being adapted for receiving a second cell culture therein;
   a second solid phase substrate in the second channel, a second biomolecule binding to the second solid phase substrate to form a second biomolecule-bound solid phase substrate;
   a second phase-gate zone having an input communicating with the second channel, the second phase-gate zone receiving an isolation buffer therein; and
   a second output zone for receiving a reagent therein; and
   wherein the force:
   urges the biomolecule-bound solid phase substrate from the channel, through the phase-gate zone and into the output zone; and
   urges the second biomolecule-bound solid phase substrate from the second channel, through the second phase-gate zone and into the second output zone.

4. A method of isolating biomolecules from cell cultures, the method comprising the steps of:
   flowing a media into a first channel;
   allowing a first cell culture to form in the first channel;
   flowing a solid phase substrate into the first channel, a biomolecule from the first cell culture binding to the solid phase substrate to form a biomolecule-bound solid phase substrate;
   drawing the biomolecule-hound solid phase substrate from the media, through an isolation buffer and into a reagent in an output zone;
   flowing a second media into a second channel, the second channel communicating with the first channel;
   allowing a second cell culture to form in the second channel;

flowing a second solid phase substrate into the second channel, a second biomolecule from the second cell culture binding to the second solid phase substrate to form a second biomolecule-bound solid phase substrate; and drawing the second biomolecule-bound solid phase substrate through a second isolation buffer and into a second output zone, the second output zone having a reagent therein.

* * * * *

UNITED STATES PATENT AND TRADEMARK OFFICE
CERTIFICATE OF CORRECTION

| | |
|---|---|
| PATENT NO. | : 8,728,410 B2 |
| APPLICATION NO. | : 13/033351 |
| DATED | : May 20, 2014 |
| INVENTOR(S) | : David J. Beebe et al. |

It is certified that error appears in the above-identified patent and that said Letters Patent is hereby corrected as shown below:

IN THE SPECIFICATION

Column 1, line 4, please add the following:

-- REFERENCE TO GOVERNMENT GRANT

This invention was made with government support under W81XWH-08-1-0525 awarded by the US Army/MRMC and CA137673 awarded by the National Institutes of Health. The government has certain rights in the invention. --

Signed and Sealed this
Twenty-first Day of October, 2014

Michelle K. Lee
*Deputy Director of the United States Patent and Trademark Office*